(12) United States Patent
Labib et al.

(10) Patent No.: US 7,772,284 B2
(45) Date of Patent: Aug. 10, 2010

(54) METHOD FOR THE TREATMENT OR PREVENTION OF VIRUS INFECTION USING POLYBIGUANIDE-BASED COMPOUNDS

(76) Inventors: Mohamed E. Labib, 650 Ewing St., Princeton, NJ (US) 08540; Richard F. Stockel, 475 Rolling Hills Rd., Bridgewater, NJ (US) 08807

( * ) Notice: Subject to any disclaimer, the term of this patent is extended or adjusted under 35 U.S.C. 154(b) by 1399 days.

(21) Appl. No.: 10/435,756

(22) Filed: Aug. 27, 2003

(65) Prior Publication Data

US 2004/0009144 A1 Jan. 15, 2004

(51) Int. Cl.
*A61K 31/505* (2006.01)
*A61K 31/155* (2006.01)
*A61K 31/40* (2006.01)
*A61K 31/41* (2006.01)
*A61K 31/415* (2006.01)
*A61K 31/425* (2006.01)
*A61K 31/47* (2006.01)
*A61K 31/74* (2006.01)
*A61K 31/785* (2006.01)
*G01N 33/53* (2006.01)
*A61P 31/04* (2006.01)
*A61P 31/18* (2006.01)

(52) U.S. Cl. .................. 514/635; 514/636; 514/275; 514/313; 514/367; 514/370; 514/383; 514/394; 514/396; 514/419; 514/634; 435/7.2; 424/78.08

(58) Field of Classification Search .............. 514/635, 514/636
See application file for complete search history.

(56) References Cited

FOREIGN PATENT DOCUMENTS

WO WO 90/00055 A1 * 1/1990
WO WO 90/04390 A1 * 5/1990
WO WO 02/17916 A1 * 3/2002

OTHER PUBLICATIONS

Merck Manual of Medical Information: 2nd Home Edition, Human Immunodeficiency Virus (HIV) Infection, pp. 1-10.*
Merck Manual of Medical Information: 2nd Home Edition, Herpes Simplex Virus (HSV) Infection, pp. 1-3.*
S. Valluri, T.P. Fleming, K.A. Laycock, I.S. Tarle, M.A. Goldberg, F.J. Garcia-Ferrer, L.R. Essary and J.S. Pepose, "In Vitro and In Vivo Effects of Polyhexamethylene Biguanide Against Herpes Simplex Virus Infection", Cornea, 1997, 16(5): 556-559.*
Sharon L. Hillier, Thomas Moench, Robin Shattock, Roberta Black, Patricia Reichelderfer and Fulvia Veronese, "In Vitro and In Vivo The Story of Nonoxynol 9", Journal of Acquired Immune Deficiency Syndromes, 2005, 39(1), 1-8.*

* cited by examiner

*Primary Examiner*—John Pak
*Assistant Examiner*—Nathan W Schlientz
(74) *Attorney, Agent, or Firm*—Michael P. Aronson

(57) ABSTRACT

An inexpensive, easily available, and convenient method of treating or preventing a virus infection is provided. The present invention relates to a method for the treatment or prevention of virus infections using polybiguanide-based compounds administering a therapeutically effective amount of a compound or a pharmaceutically acceptable salt thereof. The invention relies on the unique biochemical reaction in which polybiguanide-based compounds interfere with the spread of virus within or between organisms. The compositions and formulations described in the present invention are effective means to reduce the infectivity of the human immunodeficiency virus type 1 (HIV-1), and human herpes simplex viruses, and also to kill the causative organisms of many other sexually transmitted diseases (STDs).

7 Claims, 8 Drawing Sheets

METHOD FOR THE TREATMENT OR PREVENTION OF VIRUS INFECTION USING POLYBIGUANIDE-BASED COMPOUNDS

FIELD OF THE INVENTION

The present invention relates to polybiguanide-based compounds and a method for the treatment or prevention of viral infection using polybiguanide-based compounds.

PRIOR ART

Valluri et al. 1997 Cornea 16:556-559
Stephenson J, 2000 J. Am. Med. Assoc. 287:949
Stafford, et al. 1998 J. AIDS Hum Retroviruses 17:327-331
Bratt and Hathway, 1976 Macromolecular Chemistry 177: 2591-2605
U.K. 702,268 (Rose and Swain 11359)
U.K. 1,152,243 (Dickinson et al. 51469).
U.K. 1,167,249 (Ambler et al. Oct. 15, 1969)
U.K. 1,432,345 (Drain et al. Apr. 14, 1976)
U.K. 1,531,717 (Buckly et al. Nov. 8, 1978)
U.S. Pat. No. 4,403,078 (McCoy et al. Sep. 6, 1983)
U.S. Pat. No. 4,558,159 (McCoy et al. Dec. 10, 1985)
U.S. Pat. No. 4,891,423 (Stockel Jan. 2, 1990)
U.S. Pat. No. 5,741,886 (Stockel et al. Jul. 21, 1998)
Patent Application Publication 2003/0032768 A1 (Stockel Feb. 13, 2003).
U.S. Pat. No. 5,013,544 (Chantler and Elstein May 7, 1991)
Application Published under the PCT, International Publication Number WO 02/17916 A1 (Shetty Mar. 7, 2002)
Application Published under the PCT, International Publication Number WO 00/03682 A2 (Haces Jan. 27, 2000)

BACKGROUND OF THE INVENTION

The name polybiguanide (PBG) is used to describe a diverse group of polymers containing repeating biguanide groups and may be linear or branched. In addition the biguanide groups may part of the main chain or incorporated as side-groups or end-groups in the compound. PBGs are easily and inexpensively synthesized in large quantities and the reaction yields stable products with several potential reactive sites for further modifications. PBGs are made by the condensation polymerization of a biscyanoguanidine and a diamino compound. Typically, the final PBG product has amino and monocyanoguanidine end groups at opposite ends of a cationic polymer backbone (see FIG. 1). These end groups can be subsequently reacted with either monofunctional amino- or cyanoguanidine-containing moieties, respectively (the transferred terminal moieties are termed end-caps). Also, attaching endcaps to the polybiguanide chain can be made with other reactive groups as is known in organic chemistry. In FIG. 1, "X" is the hydrocarbon segment between the biguanide group introduced from the biscyanoguanidine monomer and "Y" is the hydrocarbon segment introduced from the diamino co-monomer. The PBG polymer (FIG. 1) lends itself to modifications and/or additions, namely: (i) size and nature of backbone segment "X," (ii) size and nature of backbone "Y," (iii) terminal amino end-cap, (iv) terminal cyanoguanidine end-cap, and (v) anions. The synthesized product possesses a distribution of molecular weights that are readily separated by HPLC, or other means, to distinct fractions with definite molecular formulae. PBGs are fully ionized at physiologic pH. Other synthesis routs may be used to produce the polybiguanide compounds by one skilled the art of organic and polymer chemistry.

Previous polybiguanides have been described in the prior art, therein there are no modified end-groups, mono end cap modification and di end cap modification (to the best of our knowledge). Representative prior art patents comprise UK patents 702,268; 1,152,243; 1,167,249; 1,432,345; and U.S. Pat. Nos. 4,403,078; 4,558,159; 4,891,423; 5,741,886; and patent application number 2003/0032768 A1.

Advantages of PBGs as HIV-1 Microbicides

PBGs are already known for their wide-spectrum antibacterial activity and safety, e.g. as a contact lens disinfectant for over thirty years (Woodcock P. M. Biguanides as Industrial Biocides. In: K. R. Payne (ed), Critical Reports on Applied Chemistry: Industrial Biocides, vol. 23 John Wiley and Sons, New York). Because of their special biological functions, these well-established low cellular toxicity compounds have potential as STD microbicides as well as conventional antiviral agents. The following features represent important technical and economic advantages of PBGs that have been noted to date: (i) high activity against a wide range of organisms even in the presence of organic matter, (ii) low mammalian toxicity (Bratt and Hathway 1976 Macromolecular Chemistry 177:2591-2605; Jangaard et al. 1968 Diabetes 17:96-104; Czyzyk et al. 1968 Diabetes 17:492-498; ICI Bulletin Cosmocil CQ—an antimicrobial agent for use in cosmetics and pharmaceuticals. ICI Americas, Inc.), (iii) absence of odor, (iv) easy handling and application, (v) chemical stability and non-volatility, (vi) no surface activity; PBGs are not surfactants, i.e. they do not lower the surface tension of water or dissolve cellular membranes like surfactants, (vii) inexpensive, (viii) easy to prepare, and (ix) greater than 96% non-metabolized (Bratt and Hathway 1976 Macromolecular Chemistry 177:2591-2605; Jangaard et al. 1968 Diabetes 17:96-104; Czyzyk et al. 1968 Diabetes 17:492-498). The starting chemicals needed to make PBGs are commercially available in large quantities and their large-scale production is straightforward. Because of the exorbitant expense of antiviral therapy in the developing world, the concept of low cost antiviral agents to prevent the transmission or to combat existing infections has emerged as one of the most paramount of needs in the world today. Effective antiviral agents having different mechanism(s) of action and low cost or low cost microbicides would be a highly desirable addition to existing therapies, especially where female control of STD would help dramatically decrease transmission.

Safety of Biguanides and PBGs:

Extensive toxicological studies, covering different exposures to tissue targets and pathways, have demonstrated the safety of PBGs (Bratt and Hathway 1976 Macromolecular Chemistry 177:2591-2605; Jangaard et al. 1968 Diabetes 17:96-104; Czyzyk et al. 1968 Diabetes 17:492-498). Notably, chlorhexidine gluconate (CHG), a bis-biguanide, has been used as a general disinfectant for over thirty years with a high level of safety (Rabe and Hillier 2000 Sex Transm Dis 27:74-78; Shubair et al. 1992 Gynecol Obstet Invest 34:229-233; Stray-Pederson et al. 1999 Int. J. Antimicrob Agents 12:245-251). Many reports support the safety of CHG in gynecology and obstetrics as a vaginal douche or as a pre-delivery vaginal wash (Shubair et al. 1992 Gynecol Obstet Invest 34:229-233; Stray-Pederson et al. 1999 Int. J. Antimicrob Agents 12:245-251). For example, Rabe and Hillier report the use of 0.25% chlorhexidine gel is safe when used vaginally against *chlamydia* (Rabe and Hillier 2000 Sex Transm Dis 27:74-78; Patton et al. 1998 Sexually Transmitted Diseases 25:421-426). With vaginal use, CHG did not disturb flora with respect to Lactobacilli species (Shubair et al. 1992

Gynecol Obstet Invest 34:229-233). Polymeric PBGs have shown less corneal toxicity, compared to CHG, especially in contact lens applications (Woodcock P. M. Biguanides as Industrial Biocides. In: K. R. Payne (ed), Critical Reports on Applied Chemistry: Industrial Biocides, vol. 23 John Wiley and Sons, New York). Further, biguanide-based drugs have excellent safety profiles as an anti-malaria drugs (Proguanil) (Leggat and Haydon 2002 J. Travel Med. 9:156-159; Chaulet et al. 2002 Arzeimittelforschung 52:407-412; Croft and Herxheimer 2002 Clin Infect Dis. discussion: 1278-1279) and for treating type 2 diabetes (Metformin) (Stepensky et al. 2002 Drug Metab. Dispos 30:861-868; Zuhri-Yafi et al. 2002 J. Pediatri Endocrinol Metab 15 Suppl 1:541-546; Wulffele et al. 2002 Br J. Clin Pharmacol 53:549 P-550P; Melikian et al. 2002 Clin Ther 24:460-467) with a daily dose of 2.5 gm. In addition Cazzanig et al. (2002 Wounds 14:169-176) and Davis et al. (2002 Wounds 14:252-256), report that polyhexamethylene biguanide can form a barrier to prevent Pseudomonas wound invasion, while Ansorg et al. (Chemotherapy 48:129-133) have tested the biguanide poly hexanide against *Staphylococcus aureus* in the nasal mucosa. Welk et al. (J. Clin. Periodontology 29:392-399) used PHMB, which has been used as an antiseptic for many years, as a mouth rinse at 0.12% and found it significantly more effective in inhibiting plaque than placebo. Therefore, the positively charged biguanide class of compounds have consistently demonstrated safety profiles that allowed for their use in human studies up to and including regulatory approvals.

Virus Inactivation mechanisms of PBGs: PBGs in general are multi-action compounds that could interfere with virus infection by interaction at the cellular or viral membrane. Their accepted biological function, as antibacterial agents, is attributed to their interaction with cell membranes, specifically anionic phospholipids and possibly proteins (Woodcock P. M. Biguanides as Industrial Biocides. In: K. R. Payne (ed), Critical Reports on Applied Chemistry: Industrial Biocides, vol. 23 John Wiley and Sons, New York; Gilbert et al. 1990 J. Appl Bacteriol 69:585-592; Broxton et al. 1984 J. Applied Bacteriol 57:115-124; Broxton et al. 1983 J. Appl Bacteriol 54:345-353; Gilbert et al. 1990 J. Appl Bacteriol 69:593-598; Broxton et al. 1984 Microbios 41:15-22).

FIG. 2 depicts the multi-level functions of PBGs as potential antiviral microbicides. First, due to their cationic nature, PBGs could retard the movement of virions by binding to their negatively charged surfaces before they reach the cell surfaces. Second, PBGs could inhibit cell-free and cell-associated virus by interacting with viral envelope lipids or negatively charged viral proteins or with low affinity cell surface receptors in a non-specific fashion. Third, PBGs could effect cross-linking of sialic acid groups of mucin and increase its viscosity and ability to function as a physical barrier to prevent infective agents from reaching the epithelium. Fourth, PBGs could bind to acidic phospholipids causing changes in lipid and protein distribution in the cell and viral membranes with the result of inhibiting viral infectivity, possibly due to dislocation or conformational changes in viral receptors or co-receptors or due to inhibiting the fusion step. Fifth, PBGs could bind specifically to high affinity virus receptors on the cell surface and therefore inhibit virus attachment, and/or fusion.

To further illustrate this last point we will present data in the examples section of this patent application that shows PBG compounds that have specific interactions with the HIV-1 co-receptors CXCR4 and CCR5. These data taken together with the recent reports of positively charged peptides binding to CXCR4 and inhibiting T cell line tropic strains of HIV (De Clercq, E. 2002 New Anti-HIV Agents and Targets. Medicinal Research Reviews 22:531-565), suggests that a similar mechanism of action is part of the polybiguanide spectrum of antiviral activity. The chemical nature of PBGs with variation in the length of the backbone linkers (X and Y in FIG. 1A) may allow for the formation of a defined three-dimensional structure that together with the positive charge characteristics of the PBG class of molecules could lead to a defined, specific mechanism of action such as that observed for the positively charged peptides (De Clercq, E. 2002 New Anti-HIV Agents and Targets. Medicinal Research Reviews 22:531-565). In addition, B. V. Shetty has disclosed a series of guanidine or biguanide compounds with antiviral and antimicrobial activity (Shetty Application Published under the PCT, International Publication Number WO 02/17916 A1, Mar. 7, 2002). It is apparent from the work of Shetty and others that positively charged compounds can be developed as antiviral agents with specific molecular targets.

Persistence—importance of PBGs binding ability: Due to their cationic nature, selected PBGs are expected to strongly interact with both free virus and cell surfaces due to the strong electrostatic interaction between PBGs and anionic phospholipid groups. We predict that these strong electrostatic interactions will ensure that dilution or washing do not readily reverse PBG binding in the vaginal environment. To minimize the effect of the cationic charge of PBGs on the overall cellular sensitivity, several strategies have been identified, including: modulating the charge density by inserting special moieties in the backbone chain, altering the pKa of the biguanide group (e.g., by substituting it with amidine, pKa=9.5 or guanidine, pKa=13.0), tailoring the chain length or end-caps and selecting their chemistry and optimizing the anion conjugated with the PBG cation. The ability to design PBGs with vastly different physical characteristics led to the identification of PEHMB (PBG in which X=2 carbon atoms and Y=6 carbon atoms in FIG. 1A) which is more potent and less toxic than all others in this class of compounds tested to date. The reason for this may lie in the nature of the three dimensional structure of PEHMB which we believe imparts on the molecule a degree of specificity in its mechanism of action. Our preliminary data indicates that of all the PBGs tested at least PEHMB interacts with cellular receptors in a specific fashion therefore, we can theorize, this specificity imparts on PEHMB a superior antiviral profile and reduced cellular toxicity with respect to other members of this class of molecule.

The present invention relates to compositions and methods for inhibiting the transmission of enveloped viruses such as alphavirus, herpes viruses (e.g. HSV-1 to HSV-8, cytomegalovirus, varicella zoster, Epstein Bar Virus, etc.), rhabdoviruses, orthomyxoviruses (e.g. influenza), retroviruses (e.g. human immunodeficiency virus type 1, HIV-1), flaviviridae (e.g. Hepatitis C, West Nile, Dengue, and yellow fever viruses), and Pox viruses (e.g. smallpox, and vaccinia viruses).

Human immunodeficiency virus type 1 (HIV-1), a member of the retrovirus family, is the causative agent in the development of acquired immune deficiency syndrome (AIDS). This condition is a catastrophic, fatal disease that presently infects millions of people worldwide. Major efforts are being made to develop novel antiviral agents with unique mechanisms of action to be used in drug therapy and on methods of preventing the transmission of HIV-1, methods of curing the AIDS disease state once contracted, and methods of ameliorating the symptoms of AIDS.

Despite almost 20 years of AIDS/HIV-1 prevention efforts and research, the sexually transmitted HIV-1 epidemic continues to be a major health problem throughout the world and is accelerating in many areas. To date the HIV epidemic has infected over 42 million people predominantly through sexual intercourse at the end of 2002. Of these there has been 3.1 cumulative deaths from the disease worldwide (from the Joint United Nations Program on HIV/AIDS and the World Health Organization's AIDS Epidemic Update Report, December 2002).

Virtually all the compounds that are currently used or are the subject of advanced clinical trials for the treatment of HIV infections belong to one of the following classes:

1) Nucleoside analogue inhibitors of reverse transcriptase functions.

2) Non-nucleoside analogue inhibitors of reverse transcriptase functions

3) HIV-1 Protease inhibitors.

4) Virus fusion inhibitors (the 36 amino acid fusion inhibitor T20 has been approved for sale by the FDA)

The HIV-1 replication cycle can be interrupted at many different points. As indicated by the approved medications the viral reverse transcriptase and protease enzymes are good molecular targets as is the entire process by which the virus fuses to and injects itself into host cells. Thus the recently approved drug T20 is the first in a novel class of anti-HIV-1 agents. However, in addition to the drugs already approved for treatment of HIV-1 infection, work continues on the discovery and development of additional treatment modalities because of the virus's propensity to mutant and thus renders ineffective the existing therapies.

At present combination therapy comprising at least three anti-HIV drugs has become the standard treatment for HIV infected patients. Virtually all drugs that have been licensed for clinical use for the treatment of HIV infection fall into one of the four categories listed above, comprising three molecular targets. However one problem with current therapy is the cost associated with the need to use multiple drugs used in combination. Estimates of $15000 to $20000 U.S. per year per person are close approximations. This cost makes it virtually impossible for many people to afford combination therapy, especially in developing nations where the need is greatest. Another problem with existing therapeutic regimens, as stated above, is the ability of the virus to develop resistance to the individual medications and many times to develop resistance to the combination therapy. This works against the population in two ways. First, the individual infected will eventually run out of treatment options and second, if the infected individual passes along a virus already resistant to many existing therapeutic agents, the newly infected individual will have a more limited treatment option than the first. Therefore, the need for new, improved and hopefully inexpensive medications is evident.

Most importantly in the search for new medications to combat the spread of the HIV-1 virus is the search for chemotherapeutic interventions that work by novel mechanism(s) of action. Several potential areas for intervention that are under consideration or have active programs in include 1) blocking the viral envelope glycoprotein gp120, 2) additional mechanisms beyond gp120 to block virus entry such as blocking the virus receptor CD4 or co-receptors CXCR4 or CCR5, 3) viral assembly and disassembly through targeting the zinc finder domain of the viral nucleo capsid protein 7 (NCp7) and 4) by interfering with the functions of the viral integrase protein, and by interruption of virus specific transcription processes.

Vaginal contraceptive products have been available for many years and usually contain nonoxynol-9 or other detergent/surfactant as the active ingredient that are toxic to cell membranes. However frequent use of N-9 causes irritation and inflammation of the vagina (M. K. Stafford et al. J. AIDS human retrovirology, 1998 17:327-331). N-9 is also toxic to vaginal and cervical cells increasing the permeability of vaginal tissue, and can inactivate lactobacilli. Lactobacilli produce lactic acid and hydrogen peroxide that serve to maintain the acidic pH of the vagina (~pH 3.5 to 5.0). At this pH, a number of sexually transmitted disease (STD) causing organisms like HIV, and spermatozoa are inactivated. Disturbance of the vaginal microbial flora can lead to vaginal infections, which in turn increase the chance of HIV/STD transmission. The most recent data (Stephenson, J. Am. Assoc. 2000, page 284-949) in which a topical formulated N-9 product strongly suggest that the compound may even enhance HIV transmission.

Therefore it is extremely important to identify and evaluate new contraceptive antimicrobial agents, microbicides, which can be used vaginally in effective doses without inactivating lactobacilli or causing overt vaginal irritation or other toxicity.

A successful microbicide should (i) be effective against infection caused by cell-free and cell-associated virus, (ii) adsorbs tightly with its molecular target(s), i.e., its adsorption should not be reversed by dilution or washing, (iii) permanently "inactivate" the virus, (iv) inactivate free virus and infected cells faster than their rate of transport through the mucus layer, (v) have persistent activity for more than one episode of coitus, (vi) be safe to host cells and tissues— causing no irritation or lesions, (vii) be easy to formulate, (viii) remain stable in the formulated state, (ix) not activate mucosal immunity, (x) retard transport in mucus and entire vaginal and rectal mucosa, and (xi) be inexpensive for worldwide application.

Current HIV-1 microbicide candidates fall into two categories—either surfactants or polyanionic compounds (Pauwels and De Clercq 1996 J. AIDS Hum Retroviruses 11:211-221; Recommendations for the development of vaginal microbicides. 1996 International Working Group on Vaginal Microbicies AIDS 10:1-6). However, these proposed agents may not satisfy all of the necessary criteria for a successful microbicide as mentioned above. In addition, most of the compounds under current investigations as microbicides are non-specific and emerged from either excipients or related compounds used in conventional topical formulations—almost none of the compounds used have definite chemical formulae, and many are based on natural or synthetic water-soluble polymers. For example, despite the effectiveness of N-9 with respect to HIV-1 inactivation in vitro, its failure to effectively prevent HIV-1 infection in vivo has been attributed to its high irritation profile and indiscriminate disruption of epithelial cells (Feldblum et al. 1986 N.C. Med J. 47:569-572; Alexander, 1990 WHO Global Programme on AIDS Fertil Steril. 54:1-18; Niruthisard et al. 1991 Sex Transm Dis 18:176-179; Roddy et al. 1993 J STD AIDS 4:165-170; Kreiss et al. JAMA 1992 268:477-482). In order to satisfy the diverse criteria stated above, the target molecule needs to be custom tailored to provide several functions at the same time. The ability to manipulate by synthetic means the molecular structure of the current classes of agents under investigation as potential microbicides (such as N-9 or C31G surfactants, or sulfated polysaccharides) is limited, or in some cases even impossible. In contrast polybiguanide-based molecules provide a wealth of possibilities with respect to targeted synthetic manipulation. These compounds are safe, inexpensive, and highly effective anti-HIV-1 microbicides that can be synthesized with or without spermicidal activity.

Herpes viruses are another class of virus that like HIV-1 develop resistance to existing therapy, and can cause problems from a STD (especially Herpes simplex virus type 2, HSV2) as well as a chronic infection point of view. For example human cytomegalovirus (HCMV) is a serious, life threatening opportunistic pathogen in immuno compromised individuals such as AIDS patients (Macher et al. 1983 NEJM 309:1454; Tyms et al. 1989 J Anitmicrob Chemother 23:89-105) or organ transplant recipients (Meyers, J. D., 1991 Am J. Med. 81:27-38). Over the past decade there has been a tremendous effort dedicated to improving the available treatments for herpes viruses. At the present time acyclovir is still the most prescribed drug for HSV1 and HSV2, while for HCMV ganciclovir, foscarnet, cidofovir, and fomivirsen are the only drugs currently available (Bedard et al. 2000 Antimicrobial Agents and Chemotherapy 44:929-937). None of the current treatments for herpesviruses are effective at preventing the sexual transmission of the viruses therefore there is still an urgent need for new drugs that have unique mechanisms of action and modes of therapeutic intervention.

SUMMARY OF THE INVENTION

The present invention provides compounds of Formula I:
And pharmaceutically acceptable salts or formulations thereof, wherein:
It can be deduced from this generalized formula that there are five different parts of the macromolecule where modifications can be performed:
(a) "Z" is an anion where said anion is a halide, carboxylate, hydroxy carboxylate, amino carboxylate, organophosphate, organophosphonate, organosulfonate, or organosulfate
(b) "A" is an amino end group while "B" is a cyanoguanidine group which can be reacted with the corresponding monoamino (reacts with the cyanoguanidino end group), or monocyanoguanidine (reacts with cyanoguanidine end group). The monoamino or monocyanoguanidine end group modifiers can be aliphatic, cycloaliphatic, heterocyclic, aryl, alkaryl, aralkyl, and oxyalkylene radicals.
(c) X and Y can be the same or different organic radical bridging groups. Suitable examples of the organic radicals represented by X and Y include C2 to C140, aliphatic, cycloaliphatic heterocyclic, aryl, alkaryl, aralkyl, and oxyalkylene radicals. X and/or Y can also be polyalkylene radical optionally interrupted by oxygen, nitrogen, or sulfur atoms, or by saturated or unsaturated cyclic nuclei.
(d) The number of repeat units for the core biguanide (n) can be 1 to 100.

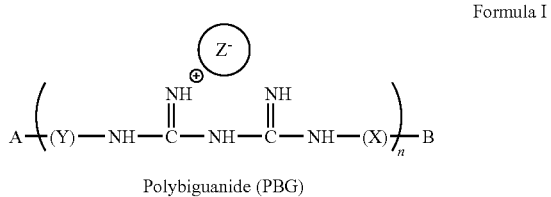

Formula I

Polybiguanide (PBG)

The present invention provides a method for treating or preventing a viral infection in a host comprising administering a therapeutically effective amount of a compound having the Formula I.

In another aspect, there is provided a pharmaceutical formulation comprising the compounds of the invention in combination with a pharmaceutically acceptable carrier or excipient.

Still another aspect, there is provided a method for treating or preventing a viral infection in a host comprising administering to the subject a combination comprising at least one compound according to Formula I and at least one further therapeutic agent.

In another aspect of the invention is the use of a compound according to Formula I, for the preparation of a medicament for treating or preventing viral infections in the host.

(B) Inhibition of viral binding was assessed after incubation of P4R5 cells with HIV-1 IIIB and the indicated compounds for 2 hr at 37° C.

Figure 4:
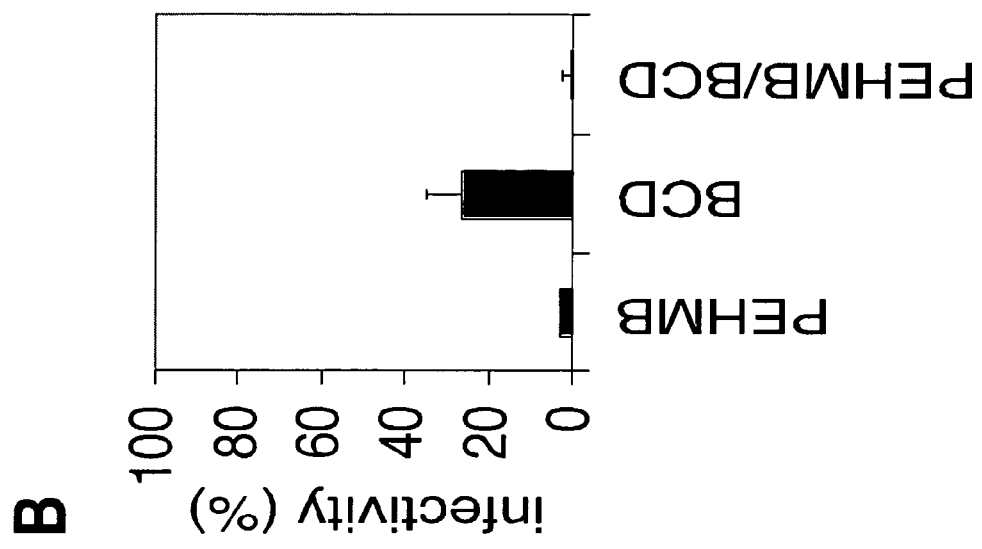
Figure 4:
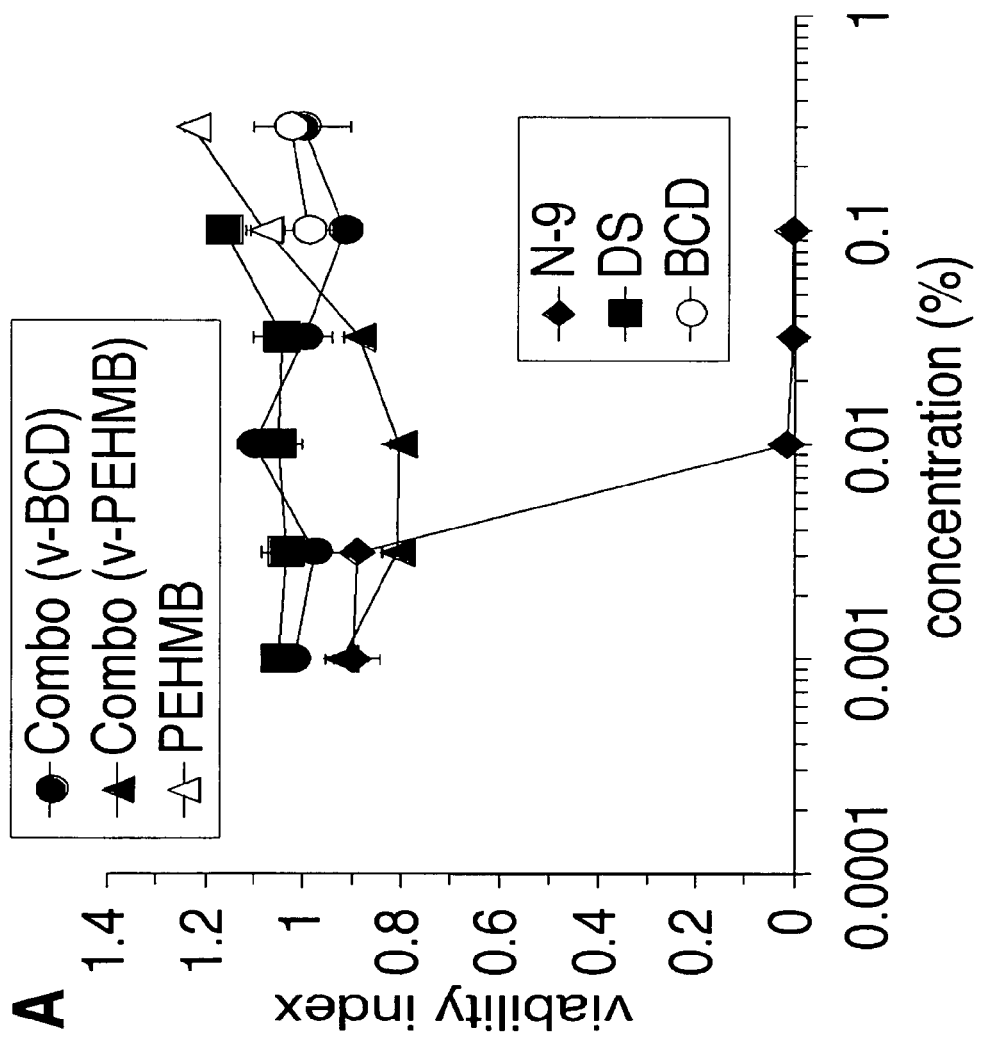

FIG. 4. A combination of PEHMB and BCD is able to inhibit HIV-1 binding and entry. (A) P4R5 cell viability was assessed by MTT assay after 2 hr exposures to the indicated compounds or compound combinations. The b-BCD combination contained 0.1% PEHMB combined with the indicated concentrations of BCD; PEHMB contained 0.3% BCD with varied amounts of PEHMB. (B) Inhibition of viral binding was assessed after incubation of P4R5 cells with HIV-1 IIIB and the PEHMB (0.1%), BCD (5 mM or approximately 0.6%), or PEHMB (0.1%)

Figure 5:
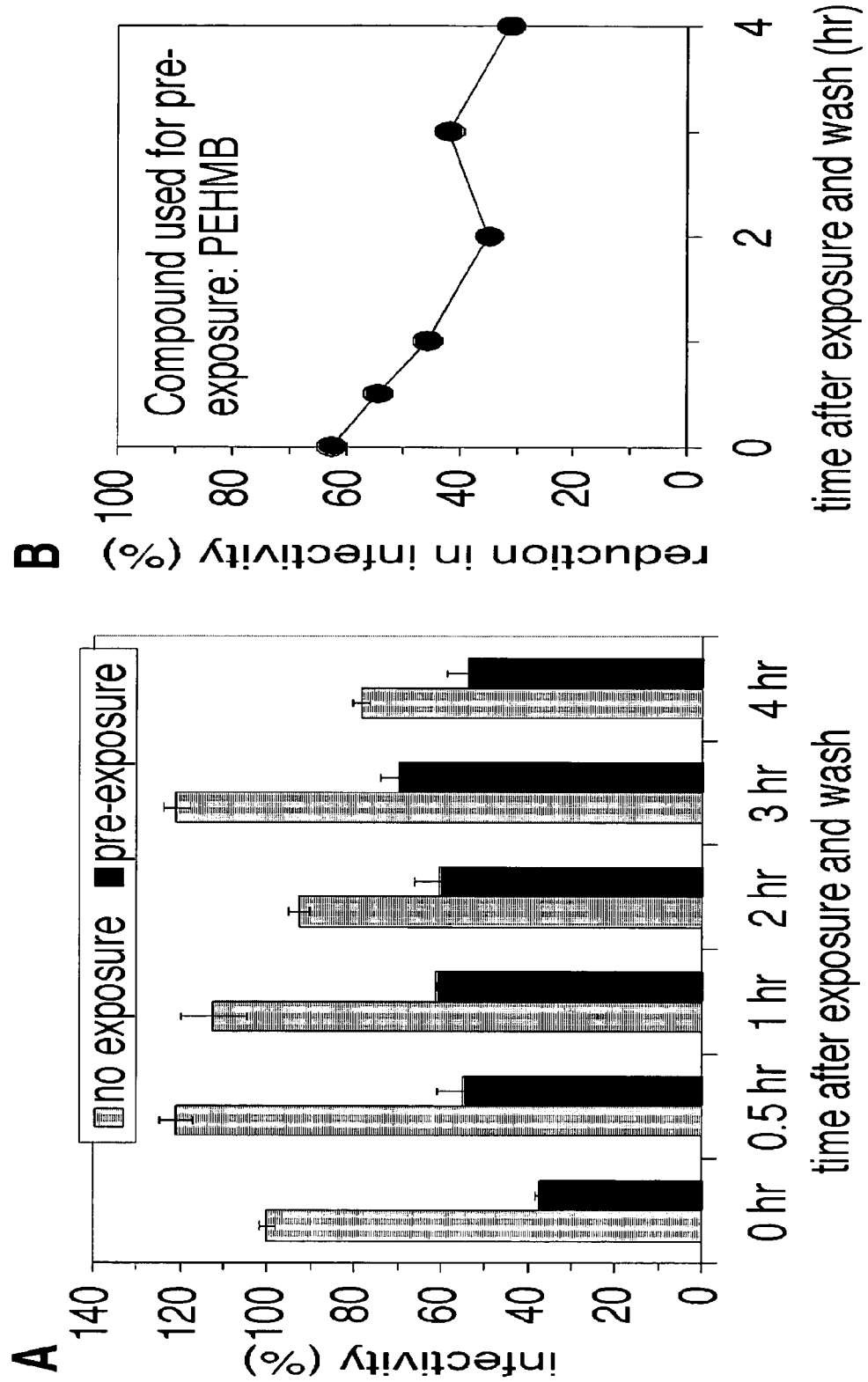

FIG. 5. PEHMB protection from HIV-1 infection persists for at least 4 hr after the compound has been removed from the media. (A) P4R5 target cells were preincubated with PEHMB (0.1%) or dextran sulfate (DS; 0.1%) for 2 hr at 37° C., washed three times with PBS, and challenged with HIV-1 IIIB (1:250, ABI) 0, 0.5, 1, 2, 3, or 4 hr after the cells were washed. Control wells were infected for 2 hr in the absence of compound, or with the simultaneous addition of PEHMB or DS. (B) The reduction in infectivity as a function of time.

Figure 6:
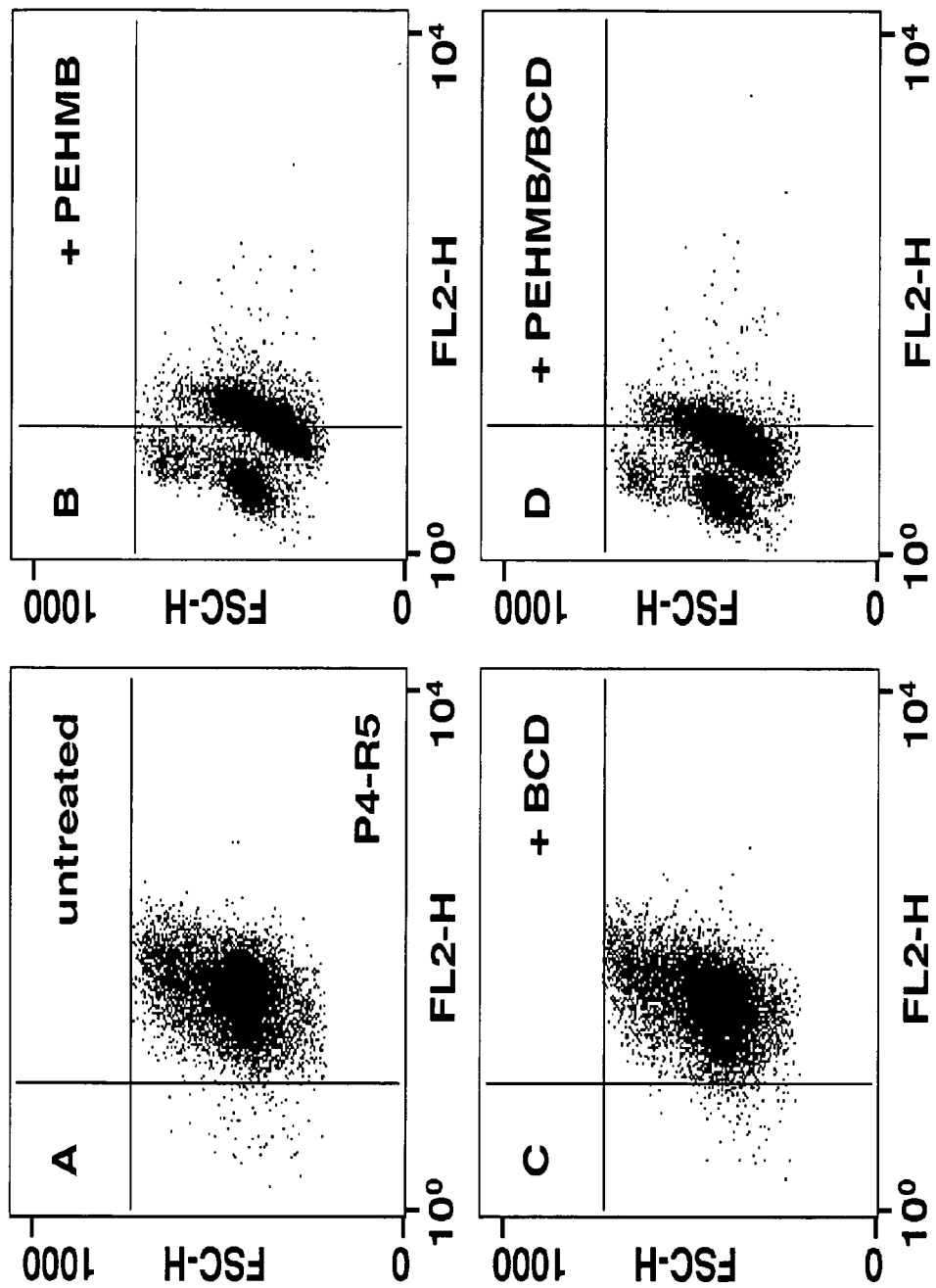

FIG. 6 HIV-1 co-receptor CXCR4 availability on the cell surface is reduced in the presence of PEHMB and a combination of PEHMB and BCD. P4—R5 cells were incubated in the absence or presence of PEHMB (0.1%), BCD (0.3%), or a mixture of both compounds (at the afore mentioned concentrations) for 2 hr at 37° C. and subsequently analyzed by FACS analysis using an antibody to CXCR4. (A) untreated; (B) PEHMB-treated; (C) BCD-treated; (D) PEHMB/BCD treated.

Figure 7:
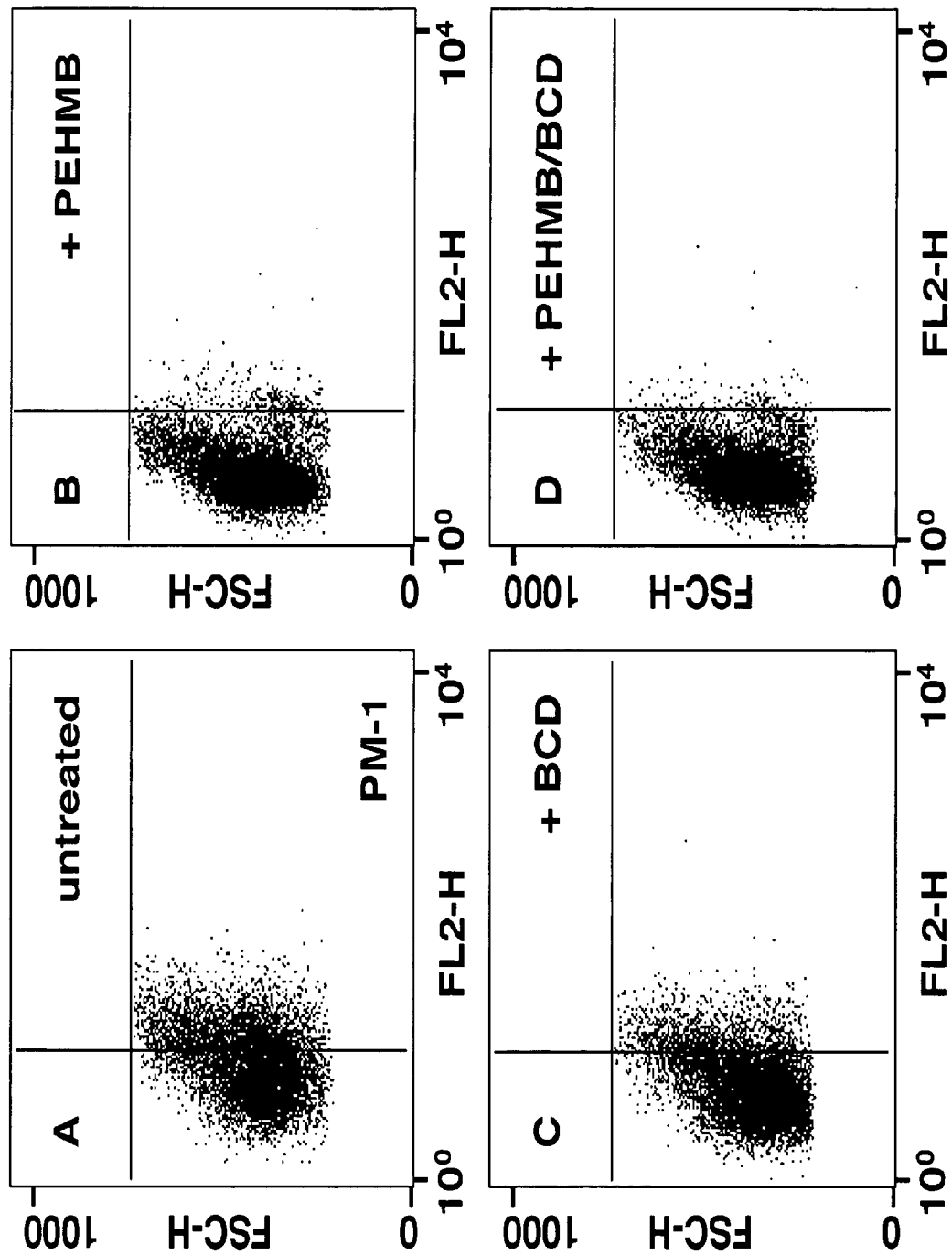

FIG. 7 HIV-1 co-receptor CXCR4 availability on the cell surface is reduced in the presence of PEHMB and a combination of PEHMB and BCD. PM-1 cells were incubated in the absence or presence of PEHMB (0.1%), BCD (0.3%), or a mixture of both compounds (at the afore mentioned concentrations) for 2 hr at 37° C. and subsequently analyzed by FACS analysis using an antibody to CXCR4. (A) untreated; (B) PEHMB-treated; (C) BCD-treated; (D) PEHMB/BCD treated.

Figure 8:
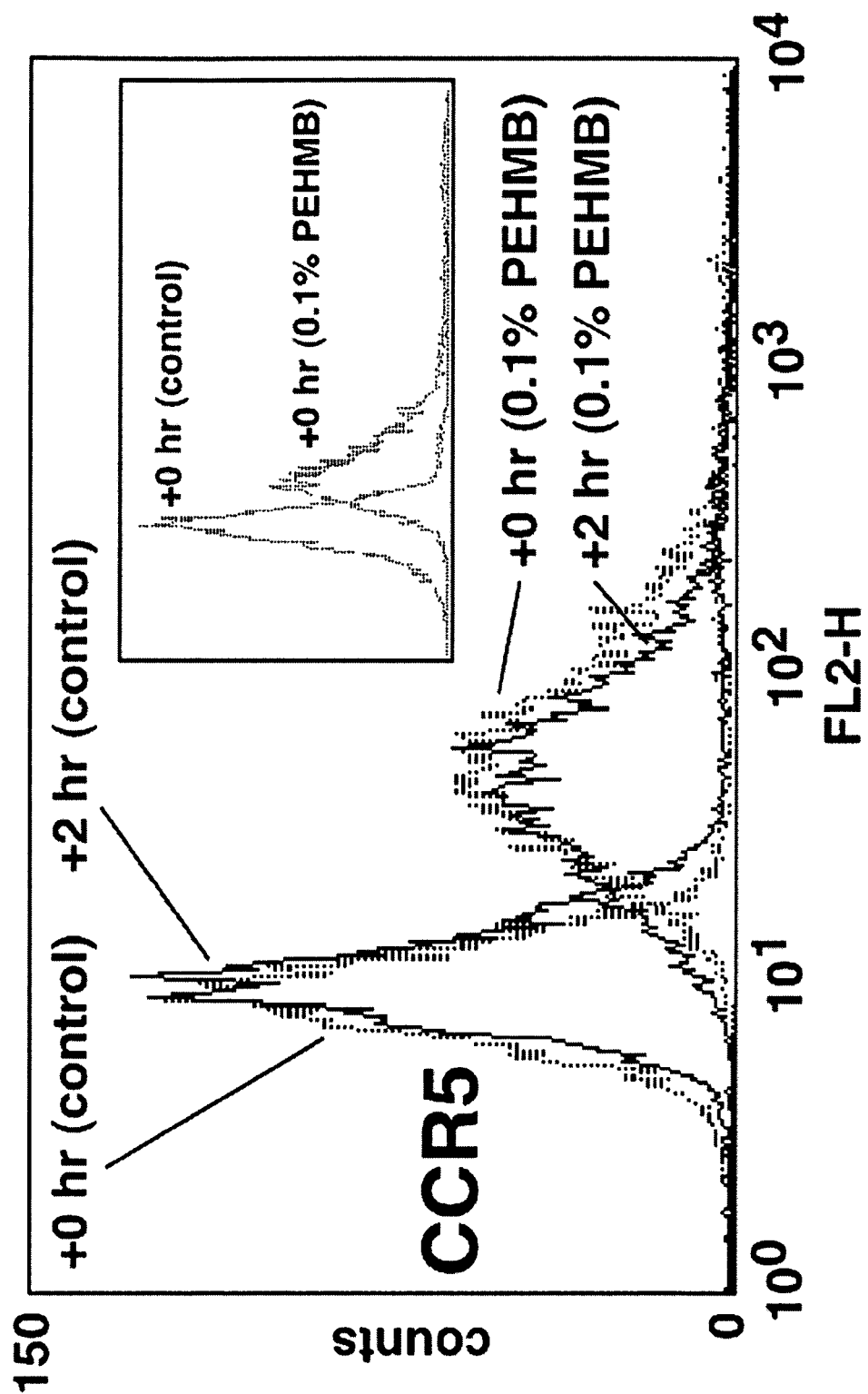

FIG. 8. Detection of CCR5 is increased by exposure of PM1 cells to PEHMB. PM-1 T cells wee incubated in the presence or absence of PEHMB (0.1% for 2 hr at 37° C.) and then analysed by FACS analysis using an anti-CCR5 antibody (R&D Systems Fab183F) either immediately (0 hr) or 2 hr post compound removal from culture media. The inset depicts the 0 hr analyses using untreated or treated cells an IgG2B isotype antibody

DETAILED DESCRIPTION OF THE INVENTION

In one embodiment of the invention the viral infection is selected from the group consisting of retrovirus infections.

In one embodiment, the retrovirus infection is selected from the group consisting of human immunodeficiency virus types 1 and 2.

In another embodiment, the retrovirus infection is human immunodeficiency virus type 1 (HIV-1).

In one embodiment of the invention the viral infection is selected from the group consisting of herpes virus infections.

In another embodiment, the herpes virus is selected from the group consisting of herpes simplex virus type 1 and herpes simplex virus type 2.

In another embodiment, the herpes virus is herpes simplex virus type 2 (HSV2).

In one embodiment, the compounds and methods of the present invention comprise those wherein the following embodiments are present, either independently or in combination:

In one aspect of the present invention, X in Formula I is an organic bridging group such as an aliphatic group containing 2 to 140 carbon atoms.

In another aspect X is $C_2$ to $C_{140}$ cycloaliphatic, heterocyclic, aryl, alkaryl, aralkyl, or oxyalkylene radicals.

In another aspect X can be a polyalkylene radical optionally interrupted by oxygen, nitrogen, or sulfur atoms, or by saturated or unsaturated cyclic nuclei.

In one aspect of the present invention, Y in Formula I is the same or different organic bridging group as X, such as an aliphatic group containing 2 to 140 carbon atoms.

In another aspect Y in Formula I is the same or different as X, and consists of C2 to C140 cycloaliphatic, heterocyclic, aryl, alkaryl, aralkyl, or oxyalkylene radicals.

In another aspect Y in Formula I can be a polyalkylene radical optionally interrupted by oxygen, nitrogen, or sulfur atoms, or by saturated or unsaturated cyclic nuclei, and can be the same or different as X.

In another aspect the number of biguanide repeat units (n in Formula I) can be one to one hundred.

In another aspect of the present invention the anion used to form the PBG salt ($Z^-$ in Formula I) could be drawn from any one or a combination of the following groups that includes halides, carboxylic acids, hydroxy carboxylic acids, amino acids, sulfonic acids, phosphonoic acids or phosphates.

In a further embodiment, the present invention relates to a method for the treatment or prevention of virus infections using polybiguanide-based compounds administering a therapeutically effective amount of a compound having the Formula I or a pharmaceutically acceptable salt thereof:

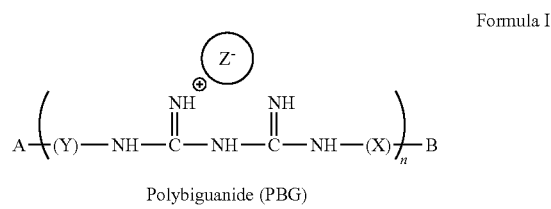

Formula I

Polybiguanide (PBG)

wherein A, B, n, X, Y, and $Z^-$ are as defined above.

In a further embodiment, the present invention relates to a method for the treatment or prevention of virus infections using polybiguanide-based compounds administering a therapeutically effective amount of a compound having the Formula I or a pharmaceutically acceptable salt thereof, wherein the virus is selected from the group of retroviruses.

In a further embodiment, the present invention relates to a method for the treatment or prevention of virus infections using polybiguanide-based compounds administering a therapeutically effective amount of a compound having the Formula I or a pharmaceutically acceptable salt thereof, wherein the virus is the human immunodeficiency virus type 1 (HIV-1).

In a further embodiment, the present invention relates to a method for the treatment or prevention of virus infections using polybiguanide-based compounds administering a therapeutically effective amount of a compound having the Formula I or a pharmaceutically acceptable salt thereof, wherein the virus is selected from the group of herpesviruses.

In a further embodiment, the present invention relates to a method for the treatment or prevention of virus infections using polybiguanide-based compounds administering a therapeutically effective amount of a compound having the Formula I or a pharmaceutically acceptable salt thereof, wherein the virus is herpes simplex virus type 2 (HSV2).

There is also provided pharmaceutically acceptable salts of the compounds of Formula I of the present invention. By the term pharmaceutically acceptable salts of the compounds of Formula I are meant those derived from pharmaceutically acceptable inorganic and organic acids. Examples of suitable acids include halides, carboxylic acids, hydroxy carboxylic acids, amino acids, sulfonic acids, phosphonoic acids or phosphates.

As used in this application, the term "alkyl" represents an unsubstituted or substituted (by a halogen, nitro, $CONH_2$, COOH, O—$C_{1-6}$ alkyl, O—$C_{2-6}$ alkynyl, hydroxyl, amino, or COOQ, wherein Q is $C_{1-6}$ alkyl; $C_{2-6}$ alkenyl; $C_{2-6}$alkynyl) straight chain, branched chain or cyclic hydrocarbon moiety (e.g. isopropyl, ethyl, fluorohexyl, or cyclopropyl). The term alkyl is also meant to include alkyls in which one or more hydrogen atoms are replaced by an halogen, more preferably, the halogen is fluoro.

The terms "alkenyl" and "alkynyl" represent an alkyl containing at least one unsaturated group (e.g. allyl).

The term hydroxy protecting group" is well known in the field of organic chemistry. Such protection groups may be found in T. Greene, *Protective Groups in Organic Synthesis*, (John Wiley and Sons, 1981). Examples of hydroxy protecting groups include but are not limited to acetyl-2-thioethyl ester, pivaloyloxymethyl ester and isopropyloxycarbonyloxymethyl ester.

The term "aryl" represents an unsaturated carbocyclic moiety, optionally mono- or di-substituted with OH, SH, amino, halogen, or $C_{1-6}$ alkyl.

The term "heteroaryl" represents an aryl wherein at least one carbon ring atom is substituted by an heteroatom (e.g. N, O, or S).

The term "aminoalkyl" represents an alkyl which is covalently bonded to the adjacent atom through a nitrogen atom.

The term "thioalkyl" represents an alkyl which is covalently bonded to the adjacent atom through a sulfur atom.

The term "alkoxy" represents an alkyl which is covalently bonded to the adjacent atom through an oxygen atom.

Halogens are chosen from F, Cl, I, and Br.

The term "host" represents any mammals including humans.

In one embodiment, the host is human.

The compounds of the present invention can be prepared by methods well know in the art. Previously polybiguanides have been described in the prior art wherein there are no modified end-groups, mono- or di-end cap modification (to the best of our knowledge). Representative prior art patents comprise UK patents 702,268; 1,152,243; 1,167,249; 1,432,345; 1,531,717; U.S. Pat. Nos. 4,403,078; 4,558,159; 4,891,423; 5,741,886; and patent application publication 2003/0032768 A1.

According to one embodiment, it will be appreciated that the amount of a compound of Formula I of the present invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will range from about 0.01 to about 750 mg/kg of body weight per day, preferably in the range of 0.5 to 60 mg/kg/day, most preferably in the range of 1 to 20 mg/kg/day for systemic administration, or for topical applications a suitable dose will range from about 0.001 to 5% wt/vol, preferably in the range of 0.1 to 1% wt/vol of formulated material.

The desired dose according to one embodiment is conveniently presented in a single dose or as a divided dose administered at appropriate intervals, for example as two, three, four or more doses per day.

In another embodiment, the compound is conveniently administered in unit dosage from; for example containing 10 to 1500 mg, conveniently 20 to 1000 mg, most conveniently 50 to 700 mg of active ingredient per unit dosage form.

According to another embodiment of the present invention, the active ingredient is administered to achieve peak plasma concentrations of the active compound of from about 1 to about 75 uM, preferably about 2 to 50 uM, most preferably 3 to 30 uM. This may be achieved, for example, by the intravenous infection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that for use in therapy a compound of Formula I of the present invention may be administered as the raw chemical, it is preferable according to one embodiment of the invention, to present the active ingredient as a pharmaceutical formulation. The embodiment of the invention thus further provides a pharmaceutical formulation comprising a compound of Formula I or a pharmaceutically acceptable salt thereof together with one or more pharmaceutically acceptable carriers thereof and, optionally, other therapeutic and/or prophylactic ingredients. The carrier(s) must be "acceptable" in the sense of being compatible with the other ingredients of the formulation and not deleterious to the recipient thereof.

According to one embodiment of the present invention, pharmaceutical formulations include but are not limited to those suitable for oral, rectal, nasal, topical, (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods according to this embodiment include the steps of bringing into association the active compound with liquid carriers or finely divided solid carriers or both and then, if necessary, shaping the product into the desired formulation.

According to another embodiment, pharmaceutical formulations suitable for oral administration are conveniently presented as discrete units such as capsules, cachets or tablets each containing a predetermined amount of the active ingredient, as a powder or granules. In another embodiment, the formulation is presented as a solution, a suspension or as an emulsion. In still another embodiment, the active ingredient is presented as a bolus, electuary or paste. Tablets and capsules for oral administration may contain conventional excipients such as binding agents, fillers, lubricants, disintegrants, or wetting agents. The tablets may be coated according to methods well know in the art. Oral liquid preparations may be in the form of, for example aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds in Formula I according to an embodiment of the present invention are formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis (mucosal or cutaneous), the compounds of Formula I, according to one embodiment of the present invention, are formulated as ointments, creams or lotions, or as transdermal patch. Such transdermal patches may contain penetration enhancers such as linalool, carvacrol, thymol, citral, menthol, and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Pharmaceutical formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

In another embodiment of the present invention a pharmaceutical formulation suitable for rectal administration consists of the active ingredient and a carrier wherein the carrier is a solid. In another embodiment, they are presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

According to one embodiment, the formulations suitable for vaginal administration are presented as pessaries, tampons, creams, gels, pastes, foams, or sprays containing in addition to the active ingredient such carriers as are known in the art to be appropriate.

For intra-nasal administration the compounds, in one embodiment of the invention, are used as a liquid spray or dispersible powder or in the form of drops. Drops may be formulated with an aqueous or non-aqueous base also comprising one or more dispersing agent, solubilising agent, or suspending agent. Liquid sprays are conveniently delivered from pressurized packs.

For administration by inhalation the compounds, according to one embodiment of the invention are conveniently delivered from an insufflator, nebulizer or pressurized pack or other convenient means of delivering an aerosol spray. In another embodiment, pressurized packs comprise a suitable propellant such as dichlorodifluoromethane, trichlorofluoromethane, dichlorotetrafluoroethane, carbon dioxide or other suitable gas. In another embodiment, the dosage unit in the pressurized aerosol is determined by providing a valve to deliver a metered amount. Alternatively, in another embodiment, for administration by inhalation or insufflation, the compounds of Formula I according to the present invention are in the form of a dry powder composition, for example a powder mix of the compound and a suitable powder base such as lactose or starch. In another embodiment, the powder composition is presented in unit dosage form in, for example, capsules or cartridges or e.g. gelatin or blister packs from which the powder may be administered with the aid of an inhalator or insufflator.

In one embodiment, the above-described formulations are adapted to give sustained release of the active ingredient.

The compounds of the invention may also be used in combination with other antiviral agents.

In one embodiment, the compounds of the invention may be employed together with at least one other antiviral agent chose from a list that includes but is not limited to antiviral protease inhibitors, polymerase inhibitors, virus/cell fusion inhibitors, integrase inhibitors, virus/cell binding inhibitors, helicase inhibitors, and/or virus binding inhibitors.

In one embodiment, the compounds of the invention may be employed together with at least one other antiviral agent chosen from amongst agents approved for use in humans by government regulatory agencies.

In one embodiment, the compounds of the invention may be employed together with at least one other antiviral agent chosen from amongst approved HIV-1 reverse transcriptase inhibitors, HIV-1 protease inhibitors, HIV-1 fusion inhibitors.

In one embodiment, the compounds of the invention may be employed together with at least one other antiviral agent chosen from amongst HIV-1 reverse transcriptase inhibitors, HIV-1 protease inhibitors, HIV-1 fusion inhibitors, HIV-1 binding inhibitors.

In one embodiment, the compounds of the invention may be employed together with at least one other antiviral agent chosen from amongst herpes virus DNA polymerase inhibitors, herpes virus protease inhibitors, herpes virus fusion inhibitors, herpes virus binding inhibitors, and ribonucleotide reductase.

In one embodiment, the compounds of the invention may be employed together with at least one other antiviral agent chosen from amongst HSV DNA polymerase inhibitors, HSV protease inhibitors, HSV fusion inhibitors, HSV binding inhibitors, and ribonucleotide reductase inhibitors.

In one embodiment, the compounds of the invention may be employed together with at least one other antiviral agent chosen from amongst acyclovir, ganciclovir, foscarnet, cidofovir, and fomivirsen.

In one embodiment, the compounds of the invention may be employed together with at least on other antiviral agent chosen from Interferon and Ribavirin.

In one embodiment, the compounds of the invention may be employed together with at least on other antiviral agent chosen from Interferon-$\alpha$ and Ribavirin.

The combinations referred to above may conveniently be presented for use in the form of a pharmaceutical formulation and thus pharmaceutical formulations comprising a combination as defined above together with a pharmaceutically acceptable carrier therefore comprise a further aspect of the invention.

The individual compounds of such combinations may be administered either sequentially or simultaneously in separate or combined pharmaceutical formulations.

When the compound of Formula I or a pharmaceutically acceptable salt or modification thereof is used in combination with a second therapeutic agent active against the same virus the dose of each compound may either be the same as or differ from that when the compound is used alone. Appropriate doses will be readily appreciated by those skilled in the art.

The following examples are provided to illustrate various embodiments of the present invention and shall not be considered as limiting in scope.

EXAMPLES

Example 1

Synthesis of Biguanide Compounds

The PBGs of this invention are readily prepared by reacting biscyanoguanides with diamino compounds in the presence of sufficient protic acids to form the polymer carried out in the neat or by using suitable solvent. The end group modifications (mono or di types) can be accomplished either by a post reaction after the initial polymer is formed, or simultaneously during the formation of the polybiguanide. All these syntheses are described in British patents numbered 1,167,249; and 1,531,717; and U.S. Pat. Nos. 4,891,423; 5,741,886; and patent application publication 2003/0032768 A1. The synthesis of mono end-capped PBGs is readily described in U.S. Pat. No. 5,741,886 while that of di-end capped PBGs is described in US 2003/0032768 A1.

The present invention provides compounds of formula (I):

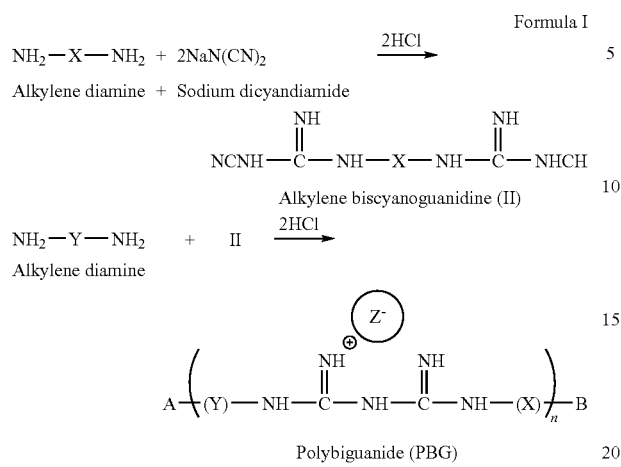

X = number of CH$_2$ groups of the biscyanoguanidine
Y = number of CH$_2$ groups of the diamine
Z$^-$ = the counter anion to form salt with PBG
A and B are potential end groups added to the PBG
n = number of biguanide repeat units The first line of the equation describes the synthesis of the biscyanoguanidine reactant, while the second shows the reaction of the diamino compound with the biscyanoguanidine compound to form the polybiguanide product as shown as Formula I. The compound in Formula I is referred to as end capped polybiguanide (PBG).

It can be deduced from this generalized formula that there are five different parts of the macromolecule where modifications can be performed:

(e) "Z" is an anion where said anion is a halide, carboxylate, hydroxy carboxylate, amino carboxylate, organophosphate, organophosphonate, organosulfonate, or organosulfate.

(f) "A" is an amino end group while "B" is a cyanoguanidine group which can be reacted with the corresponding monoamino (reacts with the cyanoguanidino end group), or monocyanoguanidine (reacts with cyanoguanidine end group). The monoamino or monocyanoguanidino end group modifiers can be aliphatic, cycloaliphatic, heterocyclic, aryl, alkaryl, aralkyl, and oxyalkylene radicals.

(g) X and Y can be the same or different organic radical bridging groups. Suitable examples of the organic radicals represented by X and Y include C2 to C140, aliphatic, cycloaliphatic heterocyclic, aryl, alkaryl, aralkyl, and oxyalkylene radicals. X and/or Y can also be polyalkylene radical optionally interrupted by oxygen, nitrogen, or sulfur atoms, or by saturated or unsaturated cyclic nuclei.

(h) The number of repeat units for the core biguanide (n) can be 1 to 100.

The compositions and method of preparation of the polybiguanides described in the cited prior art patents are thereby incorporated in the body of this invention. During our studies involving PBG's as microbicides we found that the counter ion (anion) can play an important part in the overall efficacy of the positively charged PBG. Fortunately it is quite easy to carry out the exchange of anions either by using an anion exchange resin, or by using the corresponding conjugate acid of the anion in the original synthesis when reacting the diamino reactant with the dicyanoguanidine in the presence of the desired conjugate acid, either neat or in a suitable solvent provided it has a proton which is sufficiently acidic with a pKa of about 5.0 or less. Further the anion replacement of compounds represented by Formula I can be exchanged by precipitating the free base by adding an alkali hydroxide and then neutralizing the resulting free base with the corresponding acid that carries the desired anion.

To illustrate the versatility of end-capping Table 1 lists amines, which can also represent cyanoguanides as modifiers.

TABLE 1

Common End cap modifications for polybiguanide compounds.

| Monoamine | Abbreviation | Formula |
| --- | --- | --- |
| n-octylamine | OA | NC$_8$H$_{17}$NH$_2$ |
| n-laurylamine | LA | nC$_{12}$H$_{25}$NH$_2$ |
| 2-aminothiazole | 2-AT | 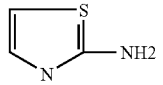 |
| 2-aminobenzimidazole | 2-ABI | 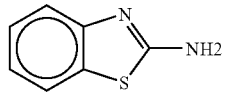 |
| 2-aminobenzothiazole | 2-ABT | 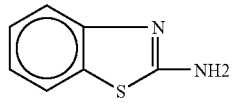 |
| 2-amino-5-chloro pyrimidine | | |
| 3-amino-1,2,4-triazole | | 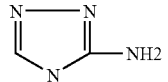 |

TABLE 1-continued

Common End cap modifications for polybiguanide compounds.

| Monoamine | Abbreviation | Formula |
|---|---|---|
| 2-(4-thiazoyl) benzimidazole | | |
| p-cholorobenzylamine | | |
| 2,4-dichloroaniline | | |
| 8-aminoquinoline | | |
| imidazole | | |
| primuline | | |
| 2-aminopyrimidine | | |
| L-tryptophan | | |
| 2-guanidinobenzimidazole | 2-GBI | benzimidazole-NHC(=NH)NH2 structure |
| Suylfonamine MNPA 1000 | * | C9H19-C6H4-(OCH2)nCH2CH(NH2)CH3 |
| Jeffamine M-2005 | ** | |

* Surfonamine MNPA and ** Jeffamine M-2005 are surface agent monamines having multiple polyoxyethylene and/or polyoxypropylene groups available from Huntsman Chemical Company It is obvious to one skilled in synthetic organic chemistry that Table 1 represents only a partial list, and that many more examples are possible provided that no other reactive functionalities are present which would compete with the primary desired reaction of forming a biguanide moiety. It is also possible for one skilled in the art to find one or more active compounds in this class by performing the above synthesis or similar methods using combinatorial synthesis or equivalent schemes by altering X, Y, or the associated anion Z. This type of experimentation is deemed obvious by adopting the systematic scientific method by one skilled in the art Example 2

Cytotoxicity Analysis of Polybiguanide Compounds

A. Monomeric Biguanides and Bis-Biguanides.

HeLa cells (ATCC designation CCL-2) were maintained in Dulbecco's Modified Eagle's medium (DMEM). P4-CCR5 (P4R5 cells) (AIDS Reagent Program #3580) were cultured in DMEM with 0.1 ug/ml puromycin as described by Charneau et al. (1994 J. Mol. Biol. 241:651-652). Sup-T1 human T lymphocytes (ATCC designation CRL-1942) were cultured in RPMI 1640. All three cell types were cultured in media supplemented with 10% fetal bovine serum (FBS), L-glutamate (0.3 mg/ml), antibiotics (penicillin, streptomycin, and kanamycin at 0.04 mg/ml each), and 0.05% sodium bicarbonate. Cells of the Vk2/E6E7 human vaginal karatinocyte cell line were cultured as described by Fichorova et al. (1997 Biol. Reprod. 57:847-855).

As part of our initial efforts to design and test PBG-based compounds optimized for cytotoxicity and anti-HIV-1 activity, experiments were performed with small molecules that contain the same biguanide group found in the higher molecular weight polybiguanides (PBGs). The experiments described below were conducted to determine the activity and cytotoxicity of short chain compounds having one or two biguanide groups. To do this HeLa cells were incubated for 2 hours in the presence of the indicated compound after which time the cells were assessed for viability using the tetrazolium dye MTT as described by Rando et al. (1995 J. Biol. Chem. 270:1754-1760). The cytotoxic concentration (CC50, concentration of compound needed to reduce cell viability after a two hour exposure by 50%) and the inhibitory concentration (IC50, concentration needed to reduce cell-free virus infectivity by 50%) are shown in Table 2. The efficacy determinations were made using P4R5 cells, which allow for the detection of bacterial β-galactosidase activity upon release of viral tat protein into the parent HeLa cell. In this assay bacterial enzyme levels are monitored colormetrically 48 hours post virus infection using a Tropix Galactro-Star machine using methods similar to those reported by Ojwang et al. (1995 Antimicrobial Agents and Chemotherapy 39:2426-2435).

TABLE 2

Cytotoxicity and efficacy of monomeric biguanides

| Chemical name | # of Biguanides | CC50 (%) | IC50 (%) |
|---|---|---|---|
| 1,1-dimethyl biguanide (metformin) | 1 | NT | NA |
| 1-phenyl biguanide | 1 | 0.150 | 0.522 |
| xyleneylene bis-biguanide | 2 | 0.385 | NA |
| hexamethylene bis-biguanide | 2 | NT | NA |
| 1-phenethyl biguanide (phenformin) | 1 | 0.538 | ND |
| nonoxynol-9 (N-9) | 0 | 0.007 | 0.005 |

Table 2. Monomeric biguanide and bis-biguanide molecules have little or no activity against cell-free HIV-1. Each entry lists the compound's chemical name, the CC50 (the concentration at which HeLa cells were reduced in viability by 50% during 2 hr exposure to the compound) and the IC50 (the concentration at which cell-free infectivity was reduced by 50% following a 2 hr exposure of cells to the compounds in the presence of virus).
NT = not toxic;
NA = No activity;
ND = Not done.

B. Toxicity of Polybiguanides.

To build on the information provided by the monomeric biguanide data a series of polybiguanide molecules were synthesized with varied linker length as described in Example 1. In these molecules the methylene spacer arms between the biguanide functionalities (X and Y in Formula I) have been changed. In this respect the nomenclature used for this series of variants is as follows: PHMB is polyhexamethylene biguanide and has six methylene groups at both the X and Y positions; hence, it is a 6-6 PBG. PHMB is FDA approved and EPA registered. In this experiment P4R5 cells (modified HeLa cells that contain HIV-1 coreceptors were incubated for 2 hours in the presence of the indicated compound after which time the cells were assessed for viability using the tetrazolium dye MTT as described by Rando et al. (1995 J. Biol. Chem. 270:1754-1760). The cytotoxic concentration (CC50, concentration of compound needed to reduce cell viability after a two-hour exposure by 50%) and the inhibitory concentration (IC50, concentration needed to reduce cell-free virus infectivity by 50%) are shown in Table 3.

TABLE 3

Cytotoxicity of PBGs with variations in linker length.

| Chemical name (X,Y)PBG | Abreviation | CC50 (%) | IC50 (%) |
|---|---|---|---|
| 2-2 PBG | PEB | >0.2 | >0.2 |
| 2-4 PBG | | | |
| 2-6 PBG | PEHMB | 0.8 | 0.004 |
| 2-8 PBG | | 0.1 | |
| 2-10 PBG | | 0.01 | |
| 2-12 | | 0.01 | |
| 3-6 | | 0.15 | 0.003 |
| 4-4 | PTMB | 0.2 | 0.0025 |
| 4-6 | | 0.05 | 0.002 |
| 6-6 | PHMB | 0.005 | 0.0015 |
| nonoxynol-9 | N-9 | 0.007 | 0.005 |

Compounds were synthesized with varied linker lengths (between the biguanide groups in the chain) to alter hydrophobicity, charge density, and chain flexibility of the backbone—smaller number of methylene linkers will limit bending and rotation of the PBG chain. For the first set of experiments, a series of compounds was synthesized with one linker shorter than the other (4-6, 3-6, and 2-6 PBG). While all of these compounds were considerably less cytotoxic than N-9 (0.003% CC50) and PHMB (0.005% CC50), there was a clear correlation between linker length and cytotoxicity (Table 3). Compared to PHMB, which was the most cytotoxic PBG compound, the other compounds were all less cytotoxic (6-6>4-6>3-6>2-6 in order of decreasing cytotoxicity). In vitro analyses demonstrated that a 2-2 PBG (a PBG with very limited chain flexibility) is non-cytotoxic up to the highest concentration tested (~0.2%). The 2-2 PBG was also not active against anti-HIV-1 in this assay system up to the highest concentration tested (~0.2%). The least cytotoxic compound in this series, the 2-6 molecule known as PEHMB (0.799% CC50, or higher based on the nature of associated anion), had no detrimental effect on cell viability at concentrations as high as 0.316%. Having identified the 2-6 PBG compound as the least cytotoxic in the above series, subsequent experiments were performed using compounds with 2-Y backbones, where Y was increased to 8, 10, or 12 methylene groups. These experiments demonstrated that the 2-8 PBG compound was less cytotoxic than either the 2-10 or 2-12, again indicating a relationship between linker length and cytotoxicity (Table 3). Cumulatively, these studies identified the 2-6 molecule (PEHMB) as the optimal compound synthesized to date with respect to in vitro cytotoxicity.

C. Toxicity of Polybiguanides with Modified Counter Anions.
See Example 3B.
D. Toxicity of Polybiguanides with Modified End Caps.
See Example 3C.
E. Toxicity of Polybiguanides in Primary Vaginal Keratinocytes.

As described above the effect of PEHMB and related compounds on P4R5 cell viability after a two-hour exposure to the compound was compared to the effects of control compounds such as N-9. In those experiments (Table 3) the PBG compounds were usually substantially less toxic than N-9. To further evaluate the effect of this class of compound on various types of cells (in particular PEHMB P4—R5 cells, ME-180 cells (ATCC HTB-33; cervical epidermoid carcinoma), VK2/E6E7 human vaginal cell line (Fichorova et al. 1997 Biol. Reprod. 57:847-855), and human primary vaginal karatinocytes (isolated from tissues obtained from vaginal reconstructive surgery)) the compounds were incubated with the different cells for various lengths of time before assessment of cell viability. The results from these experiments are presented in Table 4.

The pairing of different anions with PBGs may result in a combination that (i) has superior antiviral activity to (for example) PEHMB that uses chloride as the counter ion, (ii) imparts or introduces an additional mechanism of anti-HIV-1 activity that differs from, and complements, the activity of the PBG, or (iii) further decreases the already low cytotoxicity of the PBG. Our studies demonstrated that combining PHMB with a lactate anion (PHMB-L) resulted in a compound that was somewhat less cytotoxic than the chloride salt of PHMB. The same strategy was tested using PEHMB. In Table 4, PEHMB-L indicates PEHMB with a lactate counter anion.

The attachment of specific chemical moieties on one or both ends of PBGs also has the potential to (i) further reduce the low cytotoxicity of PBGs, (ii) augment the anti-HIV-1 activity of PBGs, and (iii) broaden the activity of PBGs by introducing additional moieties with mechanisms that will contribute anti-viral activity (possibly against additional pathogens than the PBG target). A derivative of PEHMB was synthesized with a single 1-aminoadamantane moiety on the cyanoguanidine end of the molecule (PEHMB-A).

TABLE 4

Exposure of multiple cell types for varying periods of time to PEHMB and its derivatives.

| | CC50 % | | |
|---|---|---|---|
| Cell type/compound | 10 minute exposure | 2 hr exposure | 6 hr exposure |
| P4-R5 cells | | | |
| PEHMB | 0.9 | 0.8 | 0.7 |
| PEHMB-L | 0.9 | 0.7 | 0.65 |
| PEHMB-A | 0.9 | 0.7 | 0.4 |
| N-9 | 0.2 | 0.008 | 0.005 |
| Dextran Sulfate | ~2.0 | >1.0 | >1.0 |
| ME-180 cells | | | |
| PEHMB | 2.0 | 0.6 | 0.7 |
| PEHMB-L | 1.0 | 0.6 | >1.0 |
| PEHMB-A | 1.5 | 0.6 | 0.7 |
| N-9 | 0.20 | 0.008 | 0.007 |
| Dextran Sulfate | ~2.0 | 2.0 | >1.0 |
| Vk2/E6E7 cells | | | |
| PEHMB | 1.5 | 0.9 | 0.7 |
| PEHMB-L | 1.0 | 0.9 | 0.7 |

TABLE 4-continued

Exposure of multiple cell types for varying periods of time to PEHMB and its derivatives.

| | CC50 % | | |
|---|---|---|---|
| Cell type/compound | 10 minute exposure | 2 hr exposure | 6 hr exposure |
| PEHMB-A | 1.0 | 0.3 | 0.1 |
| N-9 | 0.03 | 0.006 | 0.002 |
| Dextran Sulfate | ~2.0 | >1.0 | >1.0 |
| Primary vaginal keratinocytes | | | |
| PEHMB | | 0.2 | |
| N-9 | | 0.007 | |
| Dextran Sulfate | | 0.7 | |

Example 3

Efficacy Analysis of Polybiguanide Compounds

Antiviral assays include a viral binding/entry assay in which reporter cells such as P4R5 are incubated with virus in the presence of compound for two hours at which time the drug is washed off and the cells incubated for 48 hrs before measuring the intracellular production of β-galactosidase (Ojwang et al. 1995 Antimicrobial Agents and Chemotherapy 39:2426-2435). In cell-associated virus inhibition (CAI) assays, HIV-1 IIIB infected SUP T1 cells are pelleted to remove cell free virus and incubated with each compound for ten minutes at 37° C. before a 1:10 dilution in media and incubation with P4R5 indicator cells for 48 hours before measuring β-galactosidase activity. In cell-free virus assays HIV-1IIIB or BaL were incubated with each compound for 10 minutes at 37° C. before a 1:100 dilution in RPMI 1640, and incubated for 2 hours with P4R5 cells, and subsequent assays for viral infectivity were performed 48 hours later using the β-galactosidase method.

A. Anti-HIV-1 Efficacy of Polybiguanides.

Select compounds were assessed for their ability to inhibit events necessary for HIV-1 binding and entry. Four compounds (2-6 PBG, 3-6 PBG, 4-6 PBG, and PHMB) were able to inhibit HIV-1 IIIB binding and entry with activity equal to or greater than the control compound N-9 (0.003% IC50) but not dextran sulfate (data not shown). In these studies we compared the PBG class of compounds against representatives from the surfactant class of microbicide (N-9) and the polyanion class of compounds, dextran sulfate. All four PBG-based compounds had similar activities (0.0015% to 0.004% IC50). However, when combined with the cytotoxicity results, the 2-6 PBG compound (PEHMB) had the highest in vitro therapeutic index (200) compared to 3-6 PBG (50), 4-6 PBG (80), and N-9 (1.4). Based on numerous assays of in vitro cytotoxicity and antiviral activity, we have calculated therapeutic indices for PEHMB that range from 160 to 1000.

TABLE 5

Efficacy against HIV-1 of PBGs with variations in linker length.

| Compound | CC50 (%) | IC50 (%) | TI |
|---|---|---|---|
| 2-2 PBG (PEB) | >0.2 | >0.2 | ND |
| 2-4 PBG | | | |
| 2-6 PBG (PEHMB) | 0.8 | 0.004 | 200 |
| 2-8 PBG | 0.1 | | |

TABLE 5-continued

Efficacy against HIV-1 of PBGs with variations in linker length.

| Compound | CC50 (%) | IC50 (%) | TI |
|---|---|---|---|
| 2-10 PBG | 0.01 | | |
| 2-12 | 0.01 | | |
| 3-6 | 0.15 | 0.003 | 50 |
| 4-4 (PTMB) | 0.2 | 0.0025 | 80 |
| 4-6 | 0.05 | 0.002 | 25 |
| 6-6 (PHMB) | 0.005 | 0.0015 | 3 |
| nonoxynol-9 | 0.007 | 0.005 | 1.4 |

B. Anti-HIV-1 Efficacy and Cytotoxicity of Polybiguanides with Modified Counter Anions.

The pairing of different anions with PBGs may result in a combination that (i) has superior antiviral activity to (for example) PEHMB that uses chloride as the counter ion, (ii) imparts or introduces an additional mechanism of anti-HIV-1 activity that differs from, and complements, the activity of the PBG, or (iii) further decreases the already low cytotoxicity of the PBG. Previous studies demonstrated that combining PHMB with a lactate anion (PHMB-L) resulted in a compound that was somewhat less cytotoxic than the chloride salt of PHMB. The same strategy was tested using PEHMB. In an in vitro assay of cytotoxicity, PEHMB-L was non-cytotoxic at concentrations up to and including 0.1% (Table 4), as was PEHMB. In an assay of viral inhibition, PEHMB-L (0.054% IC50) was slightly less effective than PEHMB (0.009% IC50) (Table 6). These results indicate that (i) anion changes can affect the efficacy of the parental PBG molecular cation, and (ii) the activity of PEHMB can be supplemented or complemented by the choice of anion. The data presented in Table 6 show the results obtained after a two-hour exposure of P4R5 cells to the indicated compound in the presence of HIV-1 IIIB

TABLE 6

Efficacy against HIV-1 of PBGs with variations in counter ion.

| X–Y Compound (ion) | CC50 (%) | IC50 (%) | TI |
|---|---|---|---|
| P4R5 cell data (2 hr exposure) | | | |
| 6-6 PHMB (chloride) | 0.004 | 0.002 | 2 |
| 6-6 PHMB-L (lactate) | 0.008 | 0.003 | 2.6 |
| 2-6 PEHMB (chloride)) | 0.8 | 0.004 | 200 |
| 2-6 PEHMB (lactate) | 0.5 | 0.05 | 10 |
| Nonoxynol-9 | 0.005 | 0.005 | 1.4 |
| Vk2/E6E7 cell data (2 hr exposure) | | | |
| 6-6 PHMB (chloride) | 0.002 | | |
| 6-6 PHMB-L (lactate) | 0.005 | | |

C. Anti-HIV-1 Efficacy and Cytotoxicity of Polybiguanides with Modified End Caps.

Figure 1:
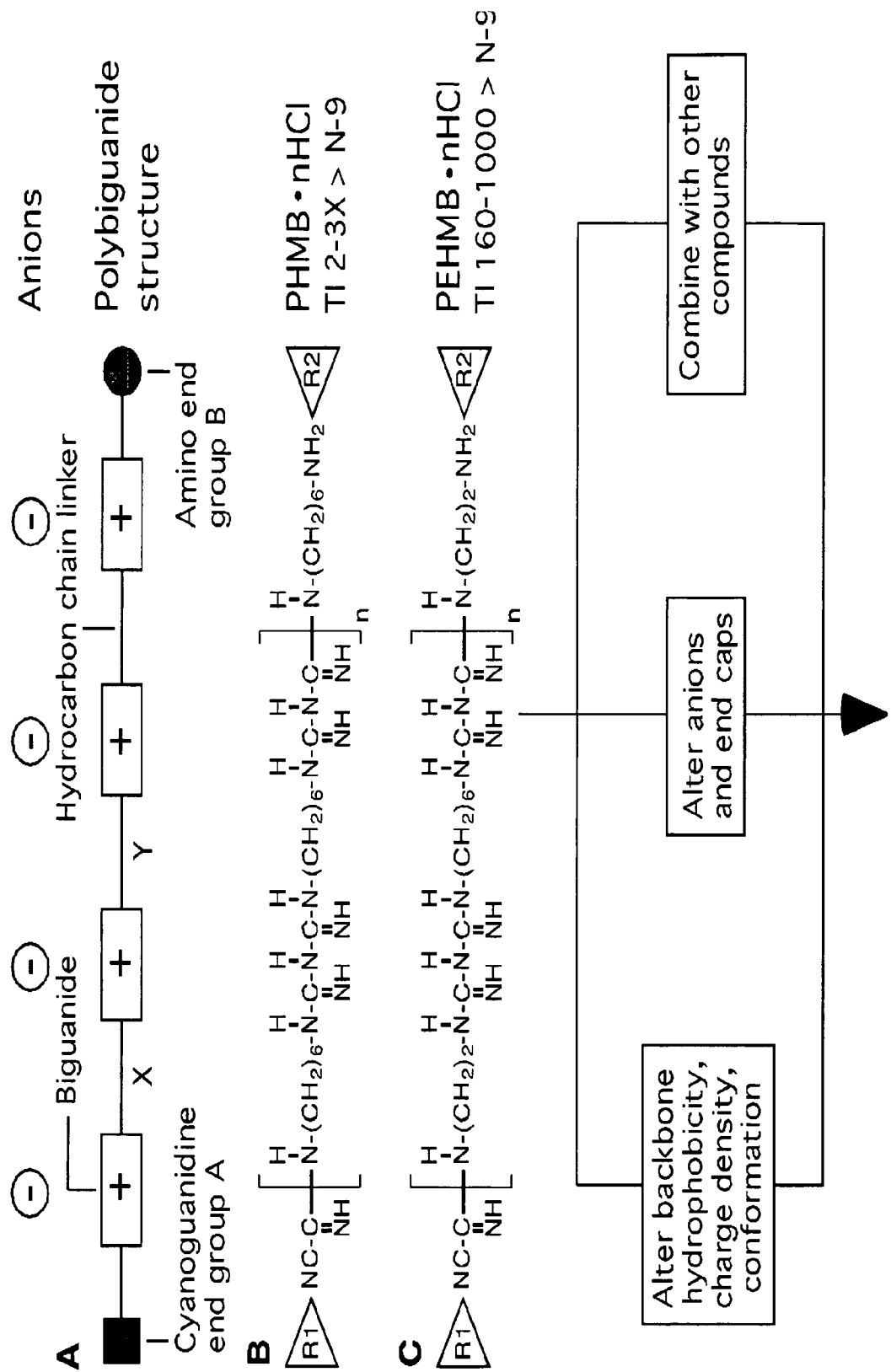
FIG. 1. PBG structures and synthesis strategies. A schematic depicting: (A) general structure of a PBG backbone with cationic biguanide groups (rectangles) separated by methylenic linker or spacers (lines); (B) formula of PHMB chloride (linkers are hexamethylene) and (C) optimized PEHMB backbone (alternating di- and hexamethylene linkers). R1 and R2 represent two end-caps although the end caps can be the same or different. The counter anion is not shown in B or C.
Figure 2:
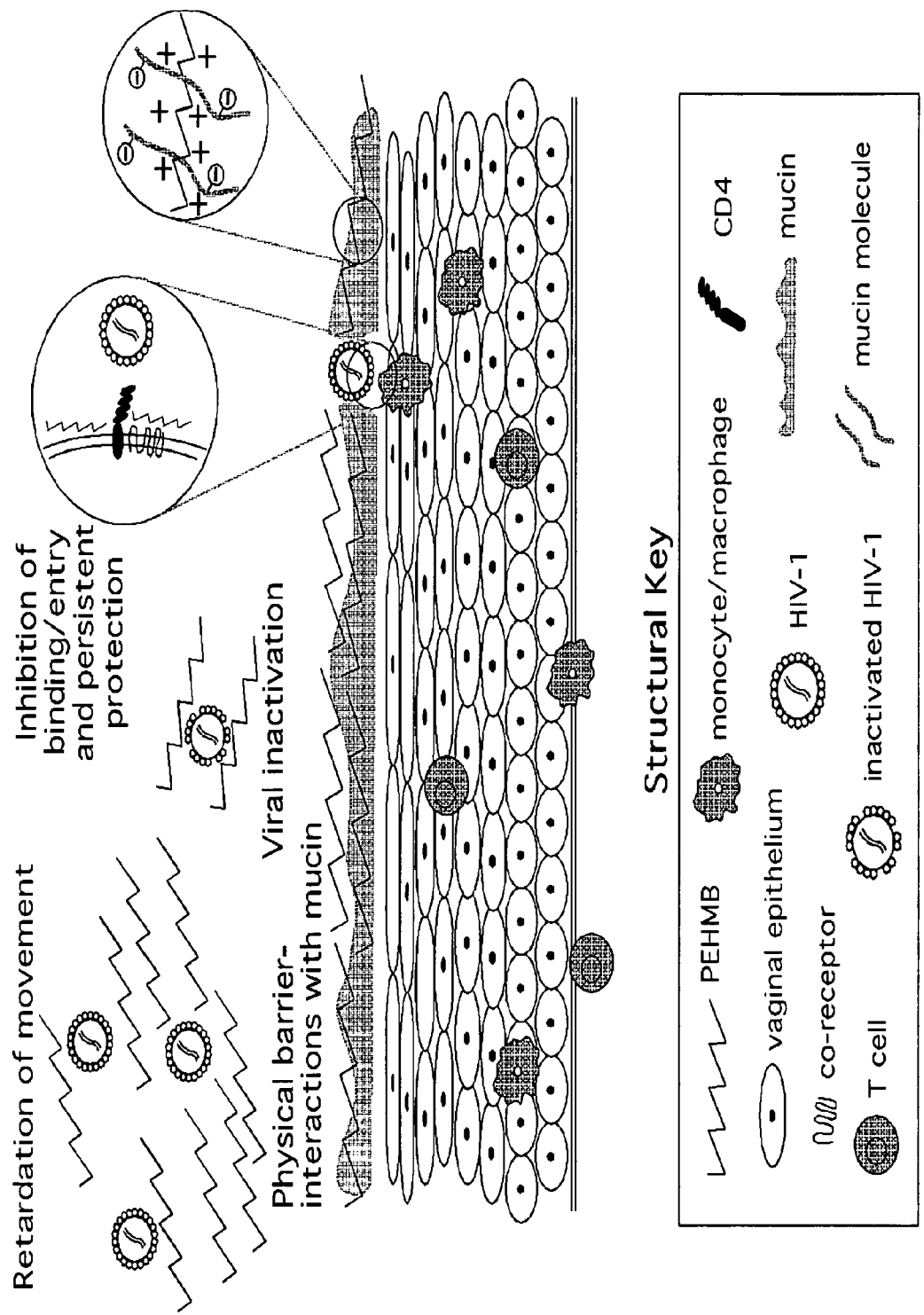
FIG. 2. PBGs have many potential sites of action. Potential anti-viral activities of PBGs include:
(i) retardation of virion and infected cell movement before reaching the epithelium,
(ii) inactivation of the virus before it reaches the cell surfaces,
(iii) electrostatic cross-linking of mucus with PBGs to form a viscous barrier over on the surface of the epithelium, and
(iv) interference with the viral binding and entry events by interacting with viral receptors/co-receptors (or inhibiting fusion).
Figure 3:
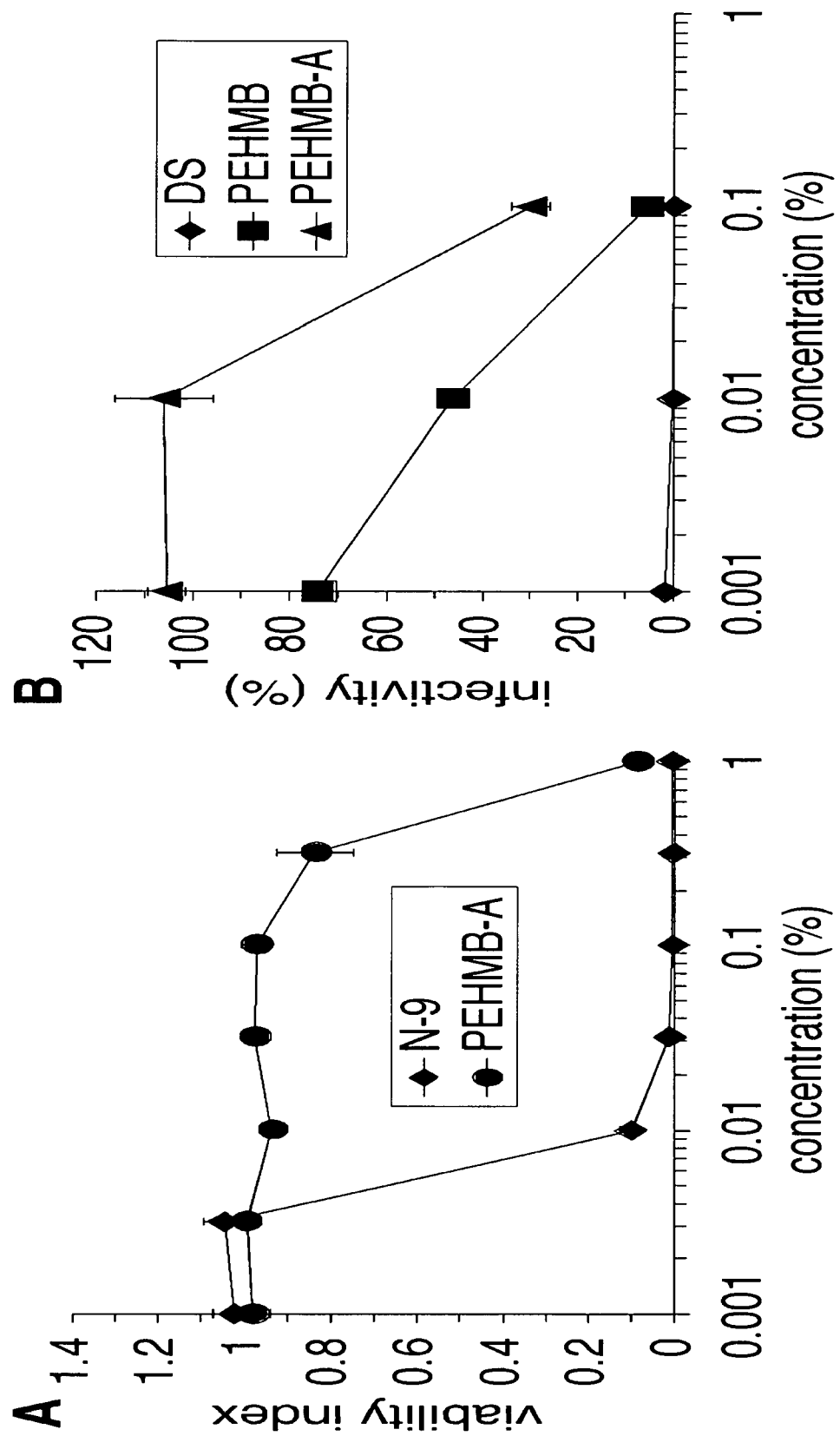
FIG. 3. Effect of end cap moiety on cellular toxicity and antiviral profile of PEHMB (A) P4R5 cell viability was assessed by MTT assay after 2 hr exposures to the indicated compounds.

The attachment of specific chemical moieties on one or both ends of PBGs also has the potential to (i) further reduce the low cytotoxicity of PBGs, (ii) augment the anti-HIV-1 activity of PBGs, and (iii) broaden the activity of PBGs by introducing additional moieties with mechanisms that will contribute anti-viral activity (possibly against additional pathogens than the PBG target). A derivative of PEHMB was synthesized with a single 1-aminoadamantane moiety on the cyanoguanidine end of the molecule (PEHMB-A). This end-cap was hypothesized to add antiviral activity to PEHMB since "amantadine" is known to have antiviral activity against other viruses (Ahmad et al. 2002, Dig. Dis Sci 47:1655-1656; Englund, et al. 2002, Semin Pediatr Infect Dis. 13:120-128;

Stilianakis et al. 2002 Lancet 359:1862-1863). In an MTT assay to evaluate cytotoxicity, the end-capped PEHMB molecule was non-cytotoxic at concentrations at or below 0.316% (0.6% CC50), and had a level of cytotoxicity similar to that of PEHMB (FIG. 3).

These data clearly show that end cap modifications can be designed and synthesized so that minimal changes in compound toxicity occur. It is likely therefore that modifications that enhance antiviral activity can also be achieved.

In this regard we have also modified the ends of PBGs using long chain hydrocarbon moieties resulting in compounds that enhanced the antiviral activity of the parent compound in cell free HIV-1 inhibition assays. Specifically we attached MNPA-1000 (Table 1) to the cyanoguanidinium end of PHMB. When PHMB (6-6 PBG) containing the MNPA-1000 end cap was tested in the cell-free virus anti-HIV-1 assays we observed an improved virus killing on the order of 10 to 100-fold. These results open up an avenue for modifications to improve the antiviral potency of PBGs. End group modifications are also critical to the overall three-dimensional shape of polymers such as PBGs, therefore the addition of hydrocarbon end caps may help stabilize these molecules in solution while also helping the PBG molecule interact with the hydrophobic portions of viral membranes. These and other end-cap modifications designed to augment the efficacy of PEHMB-based compounds will be explored in Specific Aim 1.

D. Anti-HIV-1 Efficacy of Polybiguanides in Combination with Other Compounds.

The paradigm for effective HIV-1 therapy (for systemic infections) is the use of combination drug regimens. Combination therapy has proven effective at reducing virema, delaying the onset of AIDS, and retarding the emergence of drug-resistant virus. At this time the most effective microbicide regimen has not been established. It may be that in order to block sexual transmission of HIV-1 several drugs, having different mechanisms of action will need to be applied in the same formulation. Therefore, our strategy for augmenting or broadening the spectrum of PEHMB activity is to combine PEHMB with other compounds that have different mechanisms of action against HIV-1. As an example, we have investigated the use of PEHMB combined with β-cyclodextrin (BCD), a compound that has the ability to sequester cholesterol from plasma membrane lipid rafts and down-modulate presentation of the HIV-1 co-receptor CXCR4 from the cell surface and consequently inhibit infection of HIV-1 susceptible cells (Liao et al. 2001 AIDS Res Hum Retroviruses 17:1009-1019). In vitro cytotoxicity experiments demonstrated that combinations of PEHMB and BCD, in which the concentration of one component was varied while the other was kept constant, were non-cytotoxic at the concentrations tested, as was the case for PEHMB and BCD tested alone (FIG. 4A). In an assay of viral binding inhibition using HIV-1 strain IIIB, PEHMB (0.1%) was very effective, reducing infectivity to 3% of mock-treated cells. While BCD (0.3%) also had considerable activity (27% remaining infectivity), the combination of PEHMB and BCD was equally or more effective (1% remaining infectivity) than PEHMB alone.

E. Persistent Anti-HIV-1 Efficacy of Polybiguanides.

An underlying general mechanism of the activity of PBG compounds involves electrostatic interactions with negatively charged phospholipids and with membrane-bound proteins including a direct interaction with CXCR4. We have noted that the activity of PEHMB is greater in assays of viral binding inhibition compared to experiments in which activity against cell-free virus was measured. These results suggested that PEHMB may interact more efficiently with the cellular plasma membrane compared to the viral envelope, and that this interaction may specifically disrupt events necessary for viral binding and entry, serving to protect the cells from infection. Because the interaction between PBGs and cellular membranes involves interactions with phospholipids and protein components, we hypothesized that PEHMB may provide protection from infection even after the compound has been removed from the media in which the cells are maintained. In a modified viral binding inhibition assay (VBI) assay, HIV-1-susceptible P4R5 cells were maintained for 1 or 2 hr in the presence of PEHMB (0.1% and 0.01%) and then washed extensively before challenge with HIV-1 IIIB. Despite the absence of PEHMB in the media during exposure to HIV-1, infection of PEHMB pre-treated cells (2 hr at 0.1%) was reduced to 52% compared to control cells infected without PEHMB pre-treatment (data not shown). In contrast, dextran sulfate (Dextralip 50, 0.1% or 0.01%) had no residual antiviral activity after removal of the compound from the culture media (data not shown).

Having demonstrated the persistence of antiviral activity immediately after removal of PEHMB from the media, subsequent experimentation was performed to determine the duration of the protection in the absence of compound (FIG. 5). HIV-1-susceptible target cells were incubated with PEHMB (0.1%) for 2 hr, washed extensively with PBS, and subsequently challenged with HIV-1 IIIB at 0, 0.5, 1, 2, 3, and 4 hours after washing. Introduction of virus immediately after the cells were washed resulted in a level of infection that was 37% of the infection achieved in the absence of any compound (FIG. 5A). At 30 min and 1 hr after washing the cells, the protection provided by PEHMB resulted in infections that were 45% and 55% of control levels, respectively. Even after a period of 4 hr between washing and virus challenge, residual protection provided by PEHMB pre-treatment reduced the infection to 69% of the control infection. Although the reduction in infectivity decreased over the 4 hr period, the reduction in infectivity after 4 hr was still considerable (FIG. 5B). These results indicate that PEHMB or the effect of PEHMB on cells is retained by the cells even after they have been washed.

F. Effect of Polybiguanides on HIV-1 Coreceptors CXCR4 and CCR5

To explore the hypothesis that PEHMB may affect the presentation of cell surface proteins involved in viral binding and entry events (specifically the HIV-1 co-receptors CXCR4 and CCR5), fluorescence activated cell sorting (FACS) analysis techniques were used as described by Liao et al. (2001 AIDS Res Hum Retroviruses 17:1009-1019) to document the presence of CXCR4 on the surface of target cells and to demonstrate the effect of PEHMB, BCD, and combinations of both compounds. After a 2 hr exposure to PEHMB (0.1%), P4—R5 cell presentation of CXCR4 was reduced from 98% to 29% (FIG. 6). Addition of BCD to PEHMB did result in an additional reduction in CXCR4 presentation (down to 6%), suggesting at least an additive, or possibly synergistic, effect was produced by the combination.

A similar experiment (FIG. 7) was performed using the PM-1 T lymphocyte cell line (Lusso et al. 1995 J. Virol 69:3712-3720). Incubation of PEHMB (0.1%, FIG. 7B) or BCD (0.3%, FIG. 7C) resulted in reductions of CXCR4 presentation from 45% to 5% and 22%, respectively, while the combination of PEHMB and BCD reduced expression even further (3%) (FIG. 7D). However, reductions in CD3 were not seen in response to compound exposure, indicating specificity of action with respect to PEHMB's impact on CXCR4 (data not shown). These results suggest that T cells may be more sensitive to the actions of both PEHMB and BCD, since (i) both compounds caused greater fold reductions in PM-1 CXCR4 and (ii) a reduction in CXCR4 was noted in PM-1 cells at a BCD concentration that had no apparent effect in P4—R5 cells.

Additional FACS analyses have been performed to examine the impact of PEHMB on the cell surface expression of the HIV-1 receptor CD4 and the coreceptor CCR5 in the PM-1 T cell line. These studies have indicated that PEHMB, under the conditions examined, only minimally reduced the cell surface expression levels of CD4 and CD3 (data not shown) but had a pronounced effect on CCR5 (FIG. 8). In this figure it is easy to see that treatment of cells with PEHMB dramatically increased the availability of epitopes recognized by the monoclonal antibodies used in this study suggesting a large change in the conformation of CCR5 has occurred. Therefore it is quite likely that the anti-HIV-1 effects observed for PBGs in general and PEHMB in particular is due at least in part to a disruption of virus binding to cells at the level of the viral co-receptors CXCR4 and CCR5.

G. Effect of PBGs on Herpes Simplex Virus Infections.

Herpes simplex virus plaque reduction assays were performed as described by Fennewald et al. (1995 Antiviral Research 26:37-54). This assay was a variation on the cytopathic effect assay described by Ehrlich et al. (1965 Ann N.Y. Acad. Sci. 130:5-16). Basically cells such as Vero cells are seeded onto a 96-well culture plate at approximately $1 \times 10^4$ cells/well in 0.1 ml of minimal essential medium with Earle salts supplemented with 10% heat inactivated fetal bovine serum (FBS) and pennstrep (100 U/ml penicillin G, 100 ug/ml streptomycin) and incubated at 37° C. in a 5% $CO_2$ atmosphere overnight. The medium was then removed and 50 ul of medium containing 30-50 plaque forming units (PFU) of HSV1 or HSV2, diluted in test medium and various concentrations of test compound are added to the wells. Test medium consists of MEM supplemented with 2% FBS and pennstrep. The virus was allowed to adsorb to the cells, in the presence of test compound, for 10 min at 37° C. The test medium is then removed and the cells are rinsed 3 times with fresh medium. A final 100 ul of test medium is added to the cells and the plates are returned to 37° C. Cytopathic effects are scored 40-48 hr post infection when control wells (no drug) showed maximum cytopathic effect.

In these experiments PEHMB was added to cells in the presence of HSV2 as described above for ten minutes, washed off, and the cells incubated for an additional 40-48 hrs. At this time control wells that received no drug treatment had over 300 plaques per well. Wells treated with 1% PEHMB for the indicated amount of time had less than 200 plaques per well while wells treated with 2% PEHMB had no visible plaques.

These results demonstrate that PBGs in general and PEHMB in particular are potent inhibitors of herpes simplex viruses.

The invention claimed is:

1. A method for reducing the in vitro incidence of HIV infection of P4R5 cells and human CD4(+) T-lymphocyte cell which expresses CD4 receptor and CXCR4 and/or CCR5 co-receptor comprising the step of treating said cells with an effective amount of a polyethylenehexamethylene biguanide (PEHMB) in a pharmaceutically acceptable medium.

2. A method according to claim 1 wherein the effective amount of the polyethylenehexamethylene biguanide is from 0.001% to 0.3% by weight of the medium.

3. A method according to claim 1 wherein the polyethylenehexamethylene biguanide has a Therapeutic Index, TI, in the range from 160 to 1000.

4. A method according to claim 1 wherein the polyethylenehexamethylene biguanide has one or both an amino and a monocyanoguanidine end group.

5. A method according to claim 1 wherein the polyethylenehexamethylene biguanide includes end groups selected from the group consisting of n-octylamine, n-laurylamine, 2-aminothiazole, 2-aminobenzimidazole, 2-aminobenzothiazole, 2-amino-5-chloropyrimidine, 3-amino-1,2,4-triazole, 2-(4-thiazoyl)benzimidazole, p-chlorobenzylamine, 2,4-dichloroaniline, 8-aminoquinoline, imidazole, primuline, 2-aminopyrimidine, L-tryptophan, 2-guanidinobenzimidazole and mixtures thereof.

6. A method according to claim 1 wherein the the reduction in in vitro incidence of HIV infection provided by the treatment with PEHMB persists for at least 4 hours after the PEHMB is removed from a medium in which the cells reside.

7. A method according to claim 1 wherein the pharmaceutically acceptable medium further comprises one or more antiviral agents selected from the group consisting of antiviral protease inhibitors, polymerase inhibitors, virus/cell fusion inhibitors, integrase inhibitors, virus/cell binding inhibitors, helicase inhibitors, virus binding inhibitors, HIV-1 reverse transcriptase inhibitors, HIV-1 protease inhibitors, HIV-1 fusion inhibitors, HIV-1 binding inhibitors.

* * * * *